United States Patent
Slater et al.

(10) Patent No.: US 10,201,431 B2
(45) Date of Patent: Feb. 12, 2019

(54) EXPANDABLE INTERVERTEBRAL IMPLANTS AND INSTRUMENTS

(71) Applicant: IMDS LLC, Providence, UT (US)

(72) Inventors: Nicholas Slater, Chandler, AZ (US); Justin Hyer, Smithfield, UT (US); Cortny Robison, Salt Lake City, UT (US); Joshua A. Butters, Chandler, AZ (US); Daniel J. Triplett, Providence, UT (US)

(73) Assignee: IMDS LLC, Providence, UT (US)

( * ) Notice: Subject to any disclaimer, the term of this patent is extended or adjusted under 35 U.S.C. 154(b) by 513 days.

(21) Appl. No.: 14/912,586

(22) PCT Filed: Aug. 26, 2014

(86) PCT No.: PCT/US2014/052587
§ 371 (c)(1),
(2) Date: Feb. 17, 2016

(87) PCT Pub. No.: WO2015/031291
PCT Pub. Date: Mar. 5, 2015

(65) Prior Publication Data
US 2016/0199194 A1    Jul. 14, 2016

Related U.S. Application Data

(63) Continuation of application No. 14/011,354, filed on Aug. 27, 2013, now Pat. No. 9,308,099.
(Continued)

(51) Int. Cl.
*A61F 2/44* (2006.01)
*A61F 2/46* (2006.01)
*A61F 2/30* (2006.01)

(52) U.S. Cl.
CPC ............. *A61F 2/442* (2013.01); *A61F 2/447* (2013.01); *A61F 2/4425* (2013.01);
(Continued)

(58) Field of Classification Search
CPC .......... A61F 2002/30579; A61F 2/4611; A61F 2002/4475; A61F 2/4455;
(Continued)

(56) References Cited

U.S. PATENT DOCUMENTS 619,413 A    2/1899   Higgins
4,164,225 A  8/1979   Johnson
(Continued)

FOREIGN PATENT DOCUMENTS

AU    2013206287         7/2013
AU    2013262504 B2      4/2017
(Continued)

*Primary Examiner* — Lynnsy Summitt
*Assistant Examiner* — Lynnsy Schneider
(74) *Attorney, Agent, or Firm* — Maywood IP Law; Stuart S. Bray; David Meibos

(57) ABSTRACT

Systems for interbody fusion of adjacent bone portions may include an expanding implant and related instruments. An expanding implant may be formed as a linkage which is movable between a compact configuration and an expanded configuration. A shaft of the implant may increase and decrease in length to move between the compact and expanded configurations, and an implant width perpendicular to the length may be increased in the expanded configuration. The implant width may increase more in a first direction than a second direction opposite the first direction. An inserter instrument may releasably grasp the spacer and transform the implant between the compact and expanded configurations.

15 Claims, 31 Drawing Sheets

Related U.S. Application Data

(60) Provisional application No. 61/951,001, filed on Mar. 11, 2014.

(52) U.S. Cl.
CPC .......... *A61F 2/4465* (2013.01); *A61F 2/4611* (2013.01); *A61F 2/30965* (2013.01); *A61F 2002/30013* (2013.01); *A61F 2002/3052* (2013.01); *A61F 2002/3055* (2013.01); *A61F 2002/3079* (2013.01); *A61F 2002/3083* (2013.01); *A61F 2002/30116* (2013.01); *A61F 2002/30118* (2013.01); *A61F 2002/30411* (2013.01); *A61F 2002/30471* (2013.01); *A61F 2002/30472* (2013.01); *A61F 2002/30477* (2013.01); *A61F 2002/30484* (2013.01); *A61F 2002/30509* (2013.01); *A61F 2002/30522* (2013.01); *A61F 2002/30556* (2013.01); *A61F 2002/30565* (2013.01); *A61F 2002/30566* (2013.01); *A61F 2002/30578* (2013.01); *A61F 2002/30579* (2013.01); *A61F 2002/30601* (2013.01); *A61F 2002/30629* (2013.01); *A61F 2002/30637* (2013.01); *A61F 2002/30787* (2013.01); *A61F 2002/30828* (2013.01); *A61F 2002/30878* (2013.01); *A61F 2002/4475* (2013.01); *A61F 2002/4622* (2013.01); *A61F 2002/4623* (2013.01); *A61F 2002/4627* (2013.01); *A61F 2310/00011* (2013.01); *A61F 2310/00017* (2013.01); *A61F 2310/00023* (2013.01); *A61F 2310/00029* (2013.01); *A61F 2310/00161* (2013.01); *A61F 2310/00179* (2013.01)

(58) Field of Classification Search
CPC ............ A61F 2310/00023; A61F 2/447; A61F 2002/30471; A61F 2/442; A61F 2002/4627; A61F 2002/3055; A61F 2002/30507; A61F 2/4425; A61F 2002/4415; A61F 2002/448; A61B 2017/0256; A61B 17/7065; A61B 17/8858; A61B 17/025
See application file for complete search history.

(56) References Cited

U.S. PATENT DOCUMENTS

| | | | |
|---|---|---|---|
| 4,657,550 A | 4/1987 | Daher |
| 4,834,757 A | 5/1989 | Brantigan |
| 4,863,476 A | 9/1989 | Shepperd |
| 5,059,193 A | 10/1991 | Kuslich |
| 5,171,278 A | 12/1992 | Pisharodi |
| 5,290,312 A | 3/1994 | Kojimoto |
| 5,306,310 A | 4/1994 | Siebels |
| 5,336,223 A | 8/1994 | Rogers |
| 5,390,683 A | 2/1995 | Pisharodi |
| 5,405,391 A | 4/1995 | Hednerson |
| 5,425,772 A | 6/1995 | Brantigan |
| 5,443,514 A | 8/1995 | Steffee |
| 5,458,641 A | 10/1995 | Ramirez Jimenez |
| 5,554,191 A | 9/1996 | Lahille |
| 5,571,192 A | 11/1996 | Schonhoffer |
| 5,653,762 A | 8/1997 | Pisharodi |
| 5,653,763 A | 8/1997 | Errico |
| 5,658,335 A | 8/1997 | Allen |
| 5,665,122 A | 9/1997 | Kambin |
| 5,693,100 A | 12/1997 | Pisharodi |
| 5,702,455 A | 12/1997 | Saggar |
| 5,716,415 A | 2/1998 | Steffee |
| 5,776,198 A | 7/1998 | Rabbe |
| 5,782,832 A | 7/1998 | Larsen |
| 5,865,848 A | 2/1999 | Baker |
| 5,980,522 A | 11/1999 | Koros |
| 5,989,290 A | 11/1999 | Biedermann |
| 6,015,436 A | 1/2000 | Schonhoffer |
| 6,039,761 A | 3/2000 | Li |
| 6,045,579 A | 4/2000 | Hochshuler |
| 6,080,193 A | 6/2000 | Hochshuler |
| 6,093,207 A | 7/2000 | Pisharodi |
| 6,102,950 A | 8/2000 | Vaccaro |
| 6,117,174 A | 9/2000 | Nolan |
| 6,126,689 A | 10/2000 | Brett |
| 6,126,869 A | 10/2000 | Haaland |
| 6,129,763 A | 10/2000 | Chauvin |
| 6,159,244 A | 12/2000 | Suddaby |
| 6,174,334 B1 | 1/2001 | Suddaby |
| 6,176,881 B1 | 1/2001 | Schar et al. |
| 6,183,517 B1 | 2/2001 | Suddaby |
| 6,190,413 B1 | 2/2001 | Sutcliffe |
| 6,190,414 B1 | 2/2001 | Young |
| 6,193,755 B1 | 2/2001 | Metz Stavenhagen |
| 6,193,756 B1 | 2/2001 | Studer |
| 6,193,757 B1 | 2/2001 | Foley |
| 6,200,348 B1 | 3/2001 | Biedermann |
| 6,214,050 B1 | 4/2001 | Huene |
| 6,296,647 B1 | 10/2001 | Robioneck |
| 6,299,644 B1 | 10/2001 | Vanderschot |
| 6,332,895 B1 | 12/2001 | Suddaby |
| 6,395,034 B1 | 5/2002 | Suddaby |
| 6,413,278 B1 | 7/2002 | Marchosky |
| 6,419,705 B1 | 7/2002 | Erickson |
| 6,436,140 B1 | 8/2002 | Liu |
| 6,454,806 B1 | 9/2002 | Cohen |
| 6,491,724 B1 | 12/2002 | Ferree |
| 6,562,074 B2 | 5/2003 | Gerbec |
| 6,582,431 B1 | 6/2003 | Ray |
| 6,648,917 B2 | 11/2003 | Gerbec |
| 6,660,038 B2 | 12/2003 | Boyer, II |
| 6,666,891 B2 | 12/2003 | Boehm, Jr. |
| 6,685,742 B1 | 2/2004 | Jackson |
| 6,706,070 B1 | 3/2004 | Wagner |
| 6,709,458 B2 | 3/2004 | Michelson |
| 6,723,126 B1 | 4/2004 | Berry |
| 6,730,126 B2 | 5/2004 | Boehm, Jr. |
| 6,746,484 B1 | 6/2004 | Liu |
| 6,833,006 B2 | 12/2004 | Foley |
| 6,852,129 B2 | 2/2005 | Gerbec |
| 6,863,673 B2 | 3/2005 | Gerbec |
| 6,893,464 B2 | 5/2005 | Kiester |
| 7,070,598 B2 | 7/2006 | Lim |
| 7,513,900 B2 | 4/2009 | Carrison |
| 7,625,377 B2 | 12/2009 | Veldhuizen |
| 7,799,081 B2 | 9/2010 | McKinley |
| 7,824,427 B2 | 11/2010 | Perez-Cruet |
| 7,846,206 B2 | 12/2010 | Oglaza |
| 7,879,098 B1 | 2/2011 | Simmons, Jr. |
| 7,922,729 B2 | 4/2011 | Michelson |
| 8,012,207 B2 | 9/2011 | Kim |
| 8,097,018 B2 | 1/2012 | Malandain |
| 8,097,035 B2 | 1/2012 | Glenn |
| 8,109,972 B2 | 2/2012 | Zucherman |
| 8,110,004 B2 | 2/2012 | Valdevit |
| 8,152,837 B2 | 4/2012 | Altarac |
| 8,317,798 B2 | 11/2012 | Lim |
| 8,323,344 B2 | 12/2012 | Galley |
| 8,409,291 B2 | 4/2013 | Blackwell |
| 8,491,657 B2 | 7/2013 | Attia |
| 8,496,709 B2 | 7/2013 | Schell |
| 8,506,635 B2 | 8/2013 | Palmatier |
| 8,541,355 B2 | 9/2013 | Fleckenstein |
| 8,568,481 B2 | 10/2013 | Olmos |
| 8,579,907 B2 | 11/2013 | Lim |
| 8,628,576 B2 | 1/2014 | Triplett |
| 8,652,174 B2 | 2/2014 | Gabelberger |
| 8,663,329 B2 | 3/2014 | Ernst |
| 8,678,576 B2 | 3/2014 | Edombingo et al. |
| 8,685,095 B2 | 4/2014 | Miller |
| 8,777,993 B2 | 7/2014 | Siegal |
| 8,778,027 B2 | 7/2014 | Medina |
| 8,808,385 B1 | 8/2014 | Smith |

(56) References Cited

U.S. PATENT DOCUMENTS

| | | |
|---|---|---|
| 8,900,305 B2 | 12/2014 | Stad |
| 8,926,704 B2 | 1/2015 | Glerum |
| 8,940,048 B2 | 1/2015 | Butler |
| 9,308,099 B2 | 4/2016 | Triplett |
| 9,445,918 B1 | 9/2016 | Lin et al. |
| 2001/0032017 A1 | 10/2001 | Alfaro |
| 2002/0010511 A1 | 1/2002 | Michelson |
| 2003/0229355 A1 | 12/2003 | Keller |
| 2004/0002758 A1 | 1/2004 | Landry |
| 2004/0034430 A1 | 2/2004 | Falahee |
| 2005/0177235 A1 | 8/2005 | Baynham |
| 2005/0182416 A1 | 8/2005 | Lim |
| 2005/0222681 A1 | 10/2005 | Richley |
| 2005/0234555 A1 | 10/2005 | Sutton |
| 2005/0278036 A1 | 12/2005 | Leonard |
| 2006/0142858 A1 | 6/2006 | Colleran |
| 2006/0167547 A1 | 7/2006 | Suddaby |
| 2006/0241643 A1 | 10/2006 | Lim |
| 2007/0043440 A1 | 2/2007 | William |
| 2007/0049935 A1 | 3/2007 | Edidin |
| 2007/0067034 A1 | 3/2007 | Chirico |
| 2007/0118222 A1 | 5/2007 | Lang |
| 2007/0198089 A1 | 8/2007 | Moskowitz |
| 2007/0219634 A1 | 9/2007 | Greenhalgh |
| 2007/0260315 A1 | 11/2007 | Foley |
| 2007/0282449 A1 | 12/2007 | de Villiers |
| 2008/0033440 A1 | 2/2008 | Moskowitz |
| 2008/0045968 A1 | 2/2008 | Yu |
| 2008/0082167 A1 | 4/2008 | Edidin |
| 2008/0108990 A1 | 5/2008 | Mitchell |
| 2008/0114367 A1 | 5/2008 | Meyer |
| 2008/0167657 A1 | 7/2008 | Greenhalgh |
| 2008/0183204 A1 | 7/2008 | Greenhalgh |
| 2008/0195152 A1 | 8/2008 | Altarac |
| 2008/0219604 A1 | 9/2008 | Chen et al. |
| 2008/0221686 A1 | 9/2008 | Ferree |
| 2008/0243255 A1 | 10/2008 | Butler |
| 2008/0249604 A1 | 10/2008 | Donovan |
| 2008/0281346 A1 | 11/2008 | Greenhalgh |
| 2008/0288072 A1 | 11/2008 | Kohm |
| 2008/0288078 A1 | 11/2008 | Kohm |
| 2008/0319549 A1 | 12/2008 | Greenhalgh |
| 2009/0076607 A1 | 3/2009 | Aalsma |
| 2009/0157084 A1 | 6/2009 | Aalsma |
| 2009/0198338 A1 | 8/2009 | Phan |
| 2009/0222093 A1 | 9/2009 | Liu |
| 2009/0222100 A1 | 9/2009 | Cipoletti |
| 2009/0281628 A1 | 11/2009 | Oglaza |
| 2010/0082109 A1 | 4/2010 | Greenhalgh |
| 2010/0174373 A1 | 7/2010 | Galley |
| 2010/0185291 A1 | 7/2010 | Jimenez |
| 2010/0249720 A1 | 9/2010 | Biyani |
| 2010/0286783 A1 | 11/2010 | Lechmann |
| 2010/0305705 A1 | 12/2010 | Butler |
| 2010/0318127 A1 | 12/2010 | Phan |
| 2011/0004307 A1 | 1/2011 | Ahn |
| 2011/0125270 A1 | 5/2011 | Paul |
| 2011/0172774 A1 | 7/2011 | Varela |
| 2011/0270396 A1 | 11/2011 | Leibowitz |
| 2011/0276141 A1 | 11/2011 | Caratsch |
| 2011/0282453 A1 | 11/2011 | Greenhalgh |
| 2011/0319997 A1 | 12/2011 | Glerum |
| 2012/0004732 A1 | 1/2012 | Goel |
| 2012/0053642 A1 | 3/2012 | Lozier |
| 2012/0071977 A1 | 3/2012 | Oglaza |
| 2012/0083887 A1* | 4/2012 | Purcell .................. A61F 2/447 623/17.16 |
| 2012/0083889 A1* | 4/2012 | Purcell .................. A61F 2/442 623/17.16 |
| 2012/0123546 A1 | 5/2012 | Medina |
| 2012/0136442 A1 | 5/2012 | Kleiner |
| 2012/0150241 A1 | 6/2012 | Ragab |
| 2012/0185047 A1 | 7/2012 | Wooley |
| 2012/0185049 A1 | 7/2012 | Varela |
| 2012/0209386 A1* | 8/2012 | Triplett ................ A61F 2/4465 623/17.16 |
| 2012/0215313 A1 | 8/2012 | Saidha |
| 2012/0215316 A1 | 8/2012 | Mohr |
| 2012/0226357 A1 | 9/2012 | Varela |
| 2012/0245691 A1 | 9/2012 | Reimels |
| 2013/0079882 A1 | 3/2013 | Wolfe |
| 2013/0079883 A1 | 3/2013 | Butler |
| 2013/0144391 A1 | 6/2013 | Siegal |
| 2013/0158669 A1 | 6/2013 | Sungarian |
| 2013/0190876 A1 | 7/2013 | Drochner |
| 2013/0310939 A1 | 11/2013 | Fabian |
| 2013/0325128 A1* | 12/2013 | Perloff ................ A61F 2/4455 623/17.16 |
| 2014/0031940 A1 | 1/2014 | Banouskou |
| 2014/0039622 A1 | 2/2014 | Glerum |
| 2014/0052253 A1 | 2/2014 | Perloff |
| 2014/0088714 A1 | 3/2014 | Miller |
| 2014/0121774 A1 | 5/2014 | Glerum |
| 2014/0128977 A1 | 5/2014 | Glerum |
| 2014/0172106 A1 | 6/2014 | To |
| 2014/0188224 A1 | 7/2014 | Dmuschewsky |
| 2014/0194991 A1 | 7/2014 | Jimenez |
| 2014/0194992 A1 | 7/2014 | Medina |
| 2014/0257484 A1 | 9/2014 | Flower |
| 2014/0277490 A1* | 9/2014 | Perloff .................. A61F 2/442 623/17.16 |
| 2014/0379086 A1 | 12/2014 | Elahinia |
| 2015/0012098 A1 | 1/2015 | Eastlack |
| 2015/0018951 A1 | 1/2015 | Loebl |
| 2015/0073552 A1 | 3/2015 | To |
| 2017/0056200 A1 | 3/2017 | Koch |

FOREIGN PATENT DOCUMENTS

| | | |
|---|---|---|
| CA | 2567274 C | 11/2014 |
| EP | 260044 | 3/1988 |
| EP | 1006956 A1 | 6/2000 |
| EP | 2793760 A1 | 10/2014 |
| EP | 3038566 A1 | 7/2016 |
| EP | 2729092 B1 | 9/2016 |
| EP | 2693989 B1 | 9/2017 |
| WO | WO1998034568 A1 | 8/1998 |
| WO | WO2000025706 | 5/2000 |
| WO | WO2002076335 A2 | 10/2002 |
| WO | WO2003032812 A2 | 4/2003 |
| WO | WO2005112834 A2 | 12/2005 |
| WO | WO2008070863 | 6/2008 |
| WO | WO2009037509 A1 | 3/2009 |
| WO | WO2009092102 A1 | 7/2009 |
| WO | WO2010078468 | 7/2010 |
| WO | WO2010105181 | 9/2010 |
| WO | WO2012047712 A1 | 4/2012 |
| WO | WO2012112596 A1 | 8/2012 |
| WO | WO2012141715 A1 | 10/2012 |
| WO | WO2013052807 A2 | 4/2013 |
| WO | WO2013109346 A1 | 7/2013 |
| WO | WO2013173767 A1 | 11/2013 |
| WO | WO2014144696 | 9/2014 |
| WO | WO2014151162 A1 | 9/2014 |
| WO | WO2014164625 A1 | 10/2014 |
| WO | WO2015009998 A1 | 1/2015 |
| WO | WO2015031291 A1 | 3/2015 |
| WO | WO2015063719 A1 | 3/2015 |
| WO | WO2017035155 A1 | 3/2017 |

* cited by examiner

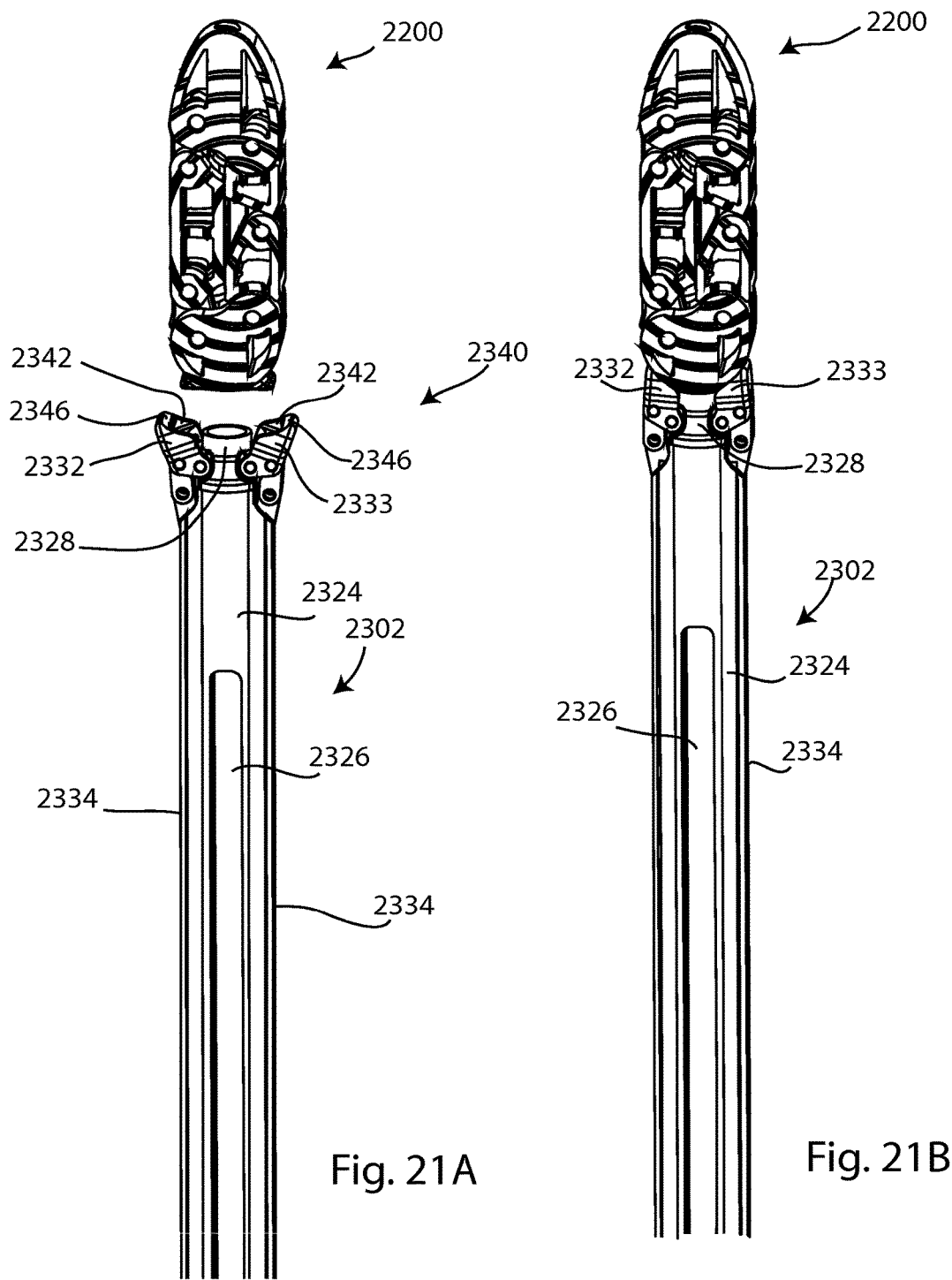

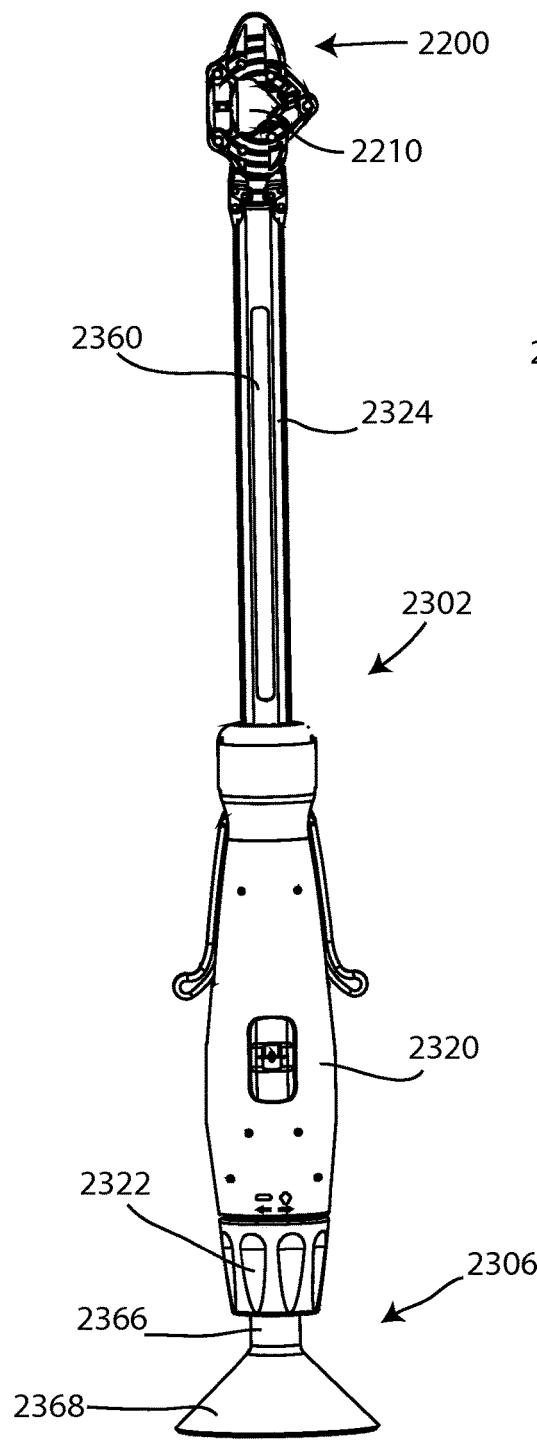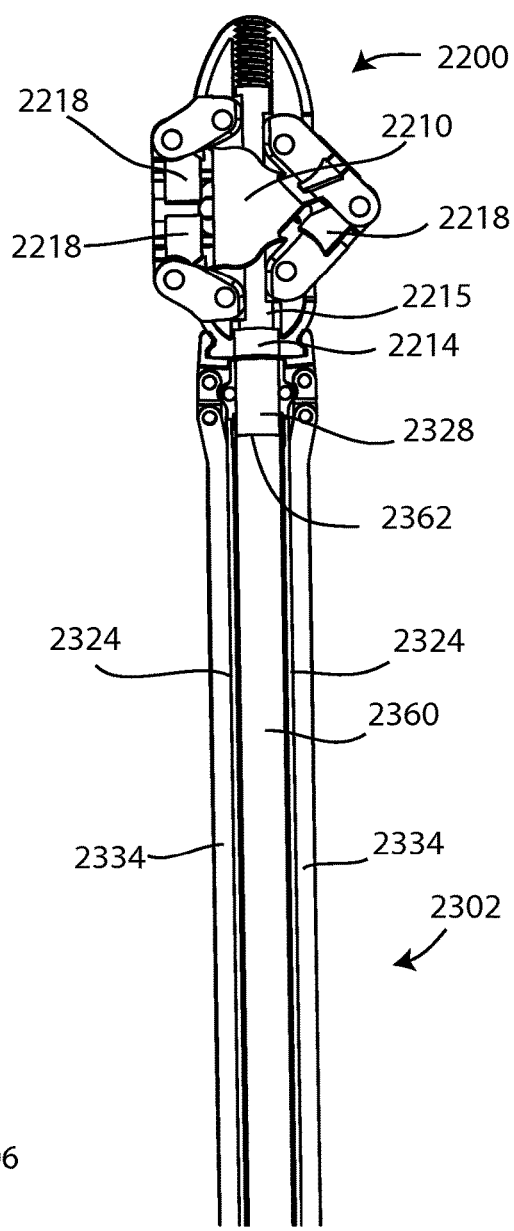
Fig. 24A
Fig. 24B

EXPANDABLE INTERVERTEBRAL IMPLANTS AND INSTRUMENTS

FIELD OF THE DISCLOSURE

The present disclosure relates to spinal fusion surgery. More precisely, the present disclosure relates to a system for stabilizing two adjacent vertebral bodies to be fused.

BACKGROUND

Intervertebral fusion may be performed to treat degenerative disc disease, spinal disc herniation, discogenic pain, spinal tumor, vertebral fracture, scoliosis, lordosis, kyphosis, spondylolisthesis, spondylosis, other degenerative spinal conditions, or any condition that causes instability of the spine. In some fusion procedures, an intervertebral implant such as a spacer or cage is placed between the vertebral bodies to provide stability. Bone graft material may be placed in the implant to promote fusion of the adjacent vertebrae.

Access to the intervertebral space between two vertebral bodies may be obtained through posterior, anterior or lateral surgical approaches. A true lateral approach requires passing through the psoas muscle to reach the intervertebral disc space. In order to minimize trauma to the muscle and the nerves in its vicinity, it may be preferable to shift the lateral trajectory anteriorly to access the anterior third of the disc space. Need exists for an implant which may be inserted from a lateral approach into the anterior portion of the disc space and expanded asymmetrically to fill the disc space.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 21A is an enlarged view of the distal end of the insertion instrument of FIG. 20, and the interbody device of FIG. 19A; FIG. 21B is an enlarged view of the interbody device of FIG. 19A mounted on the distal end of the insertion instrument of FIG. 20;

FIG. 24A is view of the insertion instrument and interbody device of FIG. 21A with the graft funnel of FIG. 20 inserted through the instrument into a channel of the interbody device, the interbody device in the expanded configuration; FIG. 24B is an enlarged cross-sectional view of the insertion instrument, graft funnel and interbody device of FIG. 24A;

DETAILED DESCRIPTION

Figure 1:
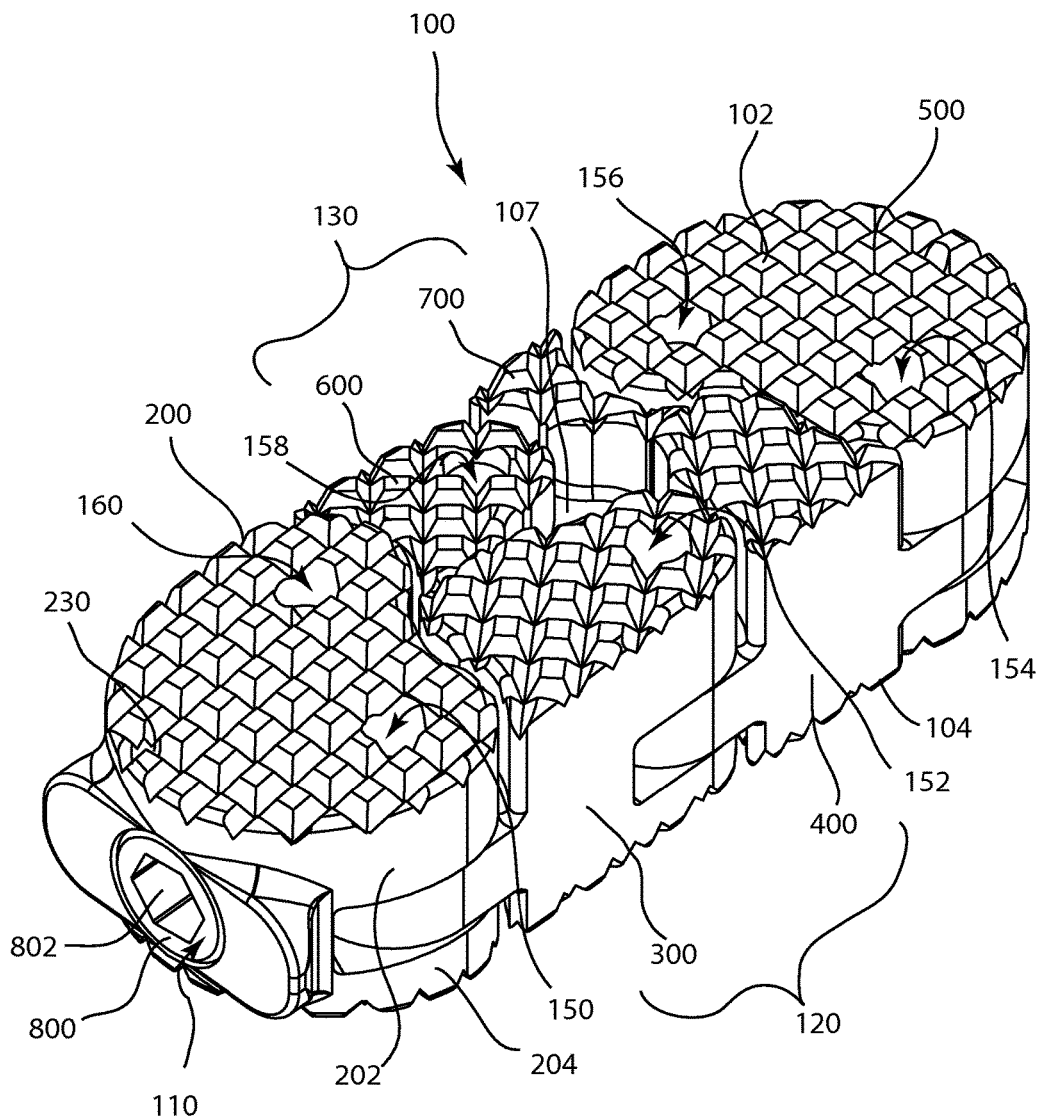
FIG. 1 is a perspective view of an expanding intervertebral fusion device in a compact configuration.
Figure 2:
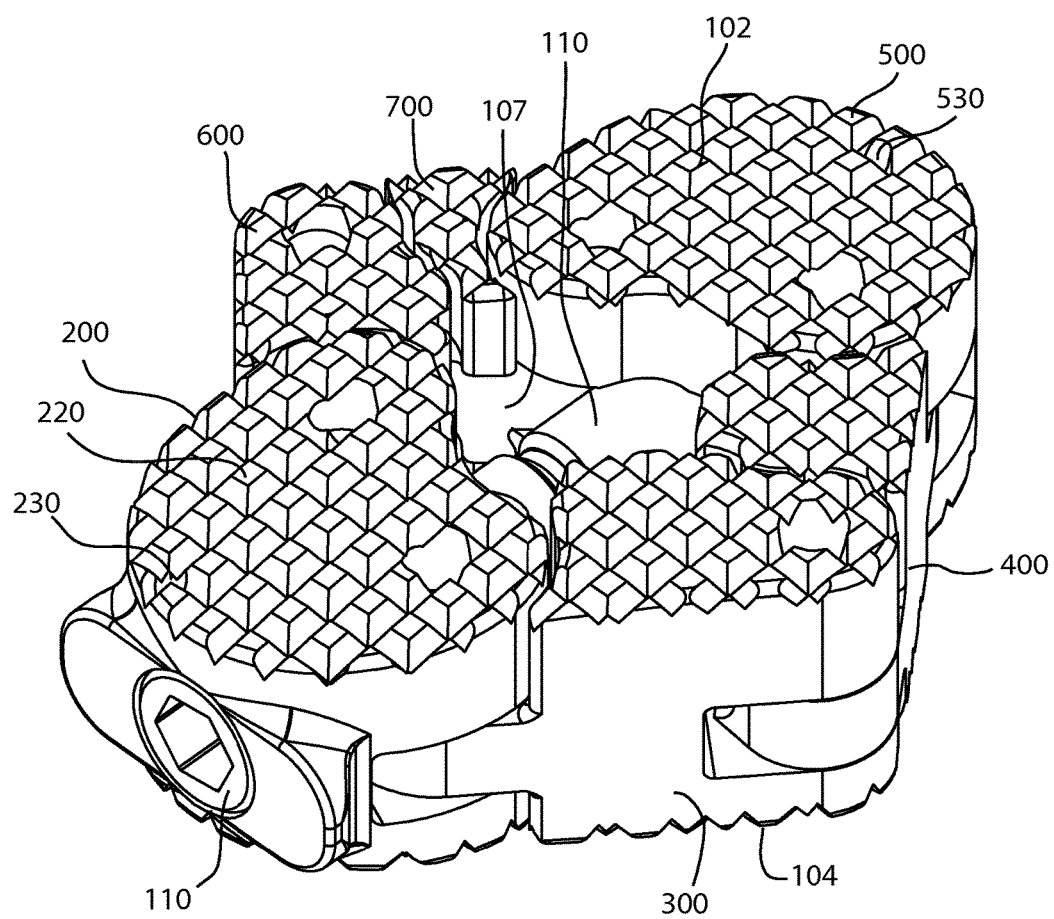
FIG. 2 is a perspective view of the fusion device of FIG. 1 in an expanded configuration.

The present disclosure provides systems, apparatus, and methods for fusion of adjacent bone portions, such as adjacent vertebral bodies in the spine. Those of skill in the art will recognize that the following description is merely illustrative of the principles of the disclosure, which may be applied in various ways to provide many different alternative embodiments. This description is made for the purpose of illustrating the general principles of this invention and is not meant to limit the inventive concepts in the appended claims. While the present disclosure is made in the context of intervertebral interbody fusion for the purposes of illustrating the concepts of the design, it is contemplated that the present design and/or variations thereof may be suited to applications outside the field intervertebral fusion. For example, the present design and/or variations thereof may be suited to applications for posterolateral fusion, or fusion of other joints.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, standard spinal anatomical terms are used with their ordinary meanings.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

According to a first aspect of the disclosure, an implant for implantation between a first vertebral body and a second vertebral body includes a first end body and a second end body; a first intermediate body and a second intermediate body, a portion of the intermediate bodies intermediate the first and second end bodies, the intermediate bodies movably joined to the first and second end bodies; a shaft coupled to and extending between the first end body and the second end body, the implant having an implant length parallel to the shaft and an implant width perpendicular to the shaft; wherein the implant is transformable between a compact configuration and an expanded configuration; wherein in the compact configuration the end bodies are spaced apart from one another; wherein in the expanded configuration the end bodies are closer to one another than in the compact configuration, the implant length is shortened relative to the compact configuration, and the implant width is increased relative to the compact configuration; wherein the increase in implant width is greater along a first direction of the implant width than along a second direction of the implant width.

Embodiments of this aspect of the disclosure may include one or more of the following features. The first direction is opposite the second direction. The first and second end bodies are irregularly shaped, and the first end body is shaped as a mirror image of the second end body. The first intermediate body moves at least partially along the first direction of the implant width from the shaft, wherein the second intermediate body moves at least partially along the second direction of the implant width from the shaft, and wherein the first intermediate body has a bone-contacting surface area greater than a bone-contacting surface area of the second intermediate body. The implant further including an implant window between the first and second intermediate bodies, wherein the size of the implant window is increased in the expanded configuration. The shaft increases and decreases in length to transform the implant between the compact configuration and the expanded configuration, wherein the implant length is equal to the shaft length in both the compact and expanded configurations. The shaft includes a screw, wherein turning the screw increases and decreases the length of the shaft. The first intermediate body includes a first arm movably joined to a second arm at an first interface, the second intermediate body includes a third arm movably joined to a fourth arm at a second interface, wherein the first and second interfaces limit the transformation of the implant into the expanded configuration and prevent over-expansion of the implant. The implant further including a spring, wherein the spring provides spring bias to urge the implant toward the expanded configuration. The implant further including a first bone-contacting side and a second bone-contacting side generally opposite the first bone-contacting side, an implant height measurable between the first bone-contacting side and the second bone-contacting side, the implant height perpendicular to the second bone-contacting side, wherein the implant height measured along the first direction of the implant width is greater than the implant height measured along the second direction of the implant width. Each of the first and second bone-contacting side including a plurality of bone-engagement features which project from each respective bone-contacting side. The implant is implantable with a tool, the tool including a tool shaft having a width, and wherein the width of the implant in the compact configuration is about equal to the width of the tool shaft; wherein the implant includes a shoulder and the tool includes a clamp having opposing jaws, wherein the jaws are engageable with the shoulder to grasp the implant; and wherein the tool includes a driving feature coaxially engageable with the implant shaft, wherein the tool is actuable to transform the implant between the compact and the expanded configurations. Each intermediate body is pivotably joined to each end body at a joint, wherein each joint includes a pin and at least one pin hole. The implant including a transverse plane, wherein each of the intermediate bodies is movably joined at a joint, wherein the joint includes joint housing and auxiliary housing, wherein the auxiliary housing strengthens the joint housing and stabilizes the implant across the transverse plane of the implant. The implant including an elongated gap between each end body and each intermediate body, wherein at least a section of the elongated gap maintains substantially the same width when the implant is in the compact configuration and when the implant is in the expanded configuration.

According to a second aspect of the disclosure, a method of implanting an implant between first and second vertebral bodies includes the steps of inserting an implant in between the first and second vertebral bodies, the implant including: a first end body and a second end body; a first intermediate body and a second intermediate body, a portion of the intermediate bodies intermediate the first and second end bodies, the intermediate bodies movably joined to the first and second end bodies; a shaft coupled to and extending between the first end body and the second end body, the implant having an implant length parallel to the shaft and an implant width perpendicular to the shaft; and transforming the implant between a compact configuration and an expanded configuration; wherein in the compact configuration the end bodies are spaced apart from one another; wherein in the expanded configuration the end bodies are closer to one another than in the compact configuration, the implant length is shortened relative to the compact configuration, and the implant width is increased relative to the compact configuration; wherein the increase in implant width is greater along a first direction of the implant width than along a second direction of the implant width.

Embodiments of this aspect of the disclosure may include one or more of the following features. Inserting the implant between the first and second vertebral bodies further includes inserting the implant along a lateral surgical approach. Inserting the implant between the first and second vertebral bodies further includes inserting the implant into the anterior third of an intervertebral disc space between the first and second vertebral bodies. The first direction of the implant width is a posterior direction and the second direction of the implant width is an anterior direction, wherein transforming the implant into the expanded configuration includes increasing the implant width greater along the posterior direction than along the anterior direction. The method further including mounting the implant on an tool; and actuating the tool to transform the implant from the compact configuration to the expanded configuration while the implant is between the first and second vertebral bodies.

Referring to FIGS. 1-9B, an expanding fusion device 100 is shown. The fusion device 100 may be an interbody fusion cage for insertion into an intervertebral disc space between adjacent vertebrae. The device 100, or implant, is constructed of multiple bodies connected together with hinge type joints formed by a plurality of pins 186, 188, 190, 192, 194, and 196, to form a linkage. The length of the implant 100 is defined by a shaft 110 which is coupled to two end bodies. The width of the implant 100 is perpendicular to the length. The implant 100 has a first bone-contacting side 102, a second bone-contacting side 104, a first edge 106 and a second edge 108. First and second edges 106, 108 may be perpendicular to the first and/or second bone-contacting sides 102, 104, or to a transverse plane dividing the implant into superior and inferior portions. An implant window 107 may be formed near the center of the implant 100.

Figure 4:
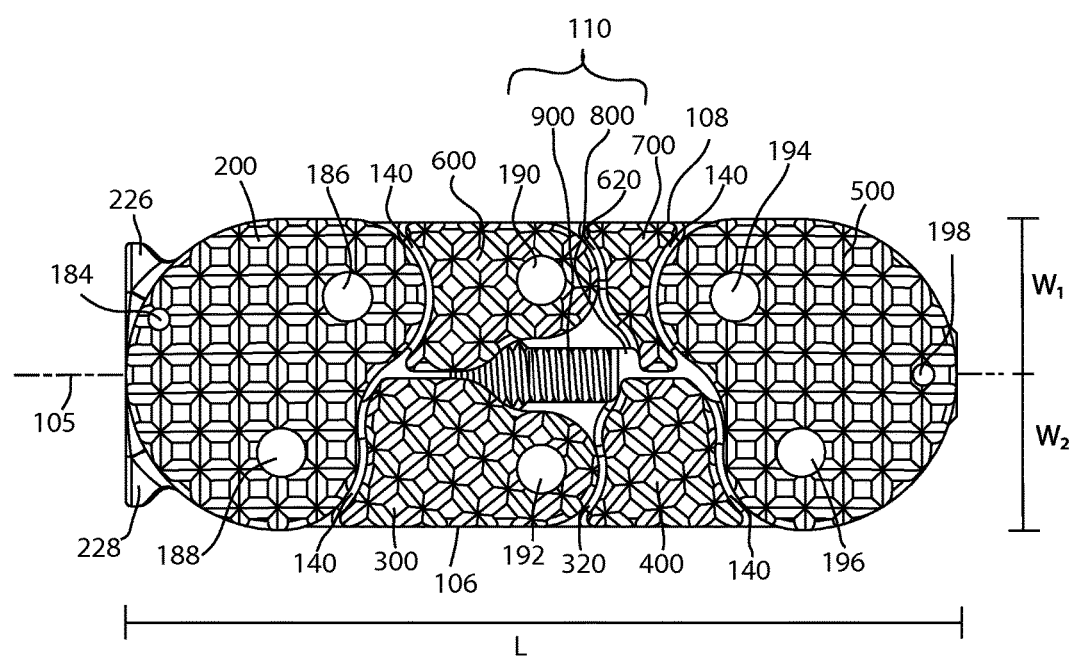
FIG. 4 is a top view of the fusion device of FIG. 1.

The implant 100 may be inserted into a disc space between two adjacent vertebrae in an initial, or compact configuration, shown in at least FIGS. 1 and 4. After insertion, the implant 100 may be reconfigured, or transformed, to a second, or expanded configuration, shown in at least FIGS. 2 and 5, that increases the width of the implant, and may increase the contact ring with the associated bone. For example, the associated bone may be vertebral endplates defining an intervertebral disc space. The implant 100 may be inserted using a lateral approach to the lumbar spine. For example, with reference to FIGS. 4 and 5, the implant 100 may be positioned in the intervertebral disc space with the pin 190 anterior, the pin 192 posterior, the pin 198 to the left, and the pin 184 to the right. In this arrangement, the expansion of the implant 100 extends the contact between the implant and the vertebral endplates in both the anterior and posterior directions, resulting in greater construct stability. In this arrangement, the first bone-contacting side 102 may be an upper, or superior side of the implant and the second bone-contacting side 104 may be a lower, or inferior side. In this arrangement, first edge 106 may be a posterior edge and second edge 108 may be an anterior edge.

Referring to FIGS. 1-4, implant 100 includes a first end body 200 and a second end body 500, each end body coupled to a portion of the shaft 110. Each end body may be irregularly shaped, and the shape of the one end body may be a mirror image of the shape of the other end body. In the embodiment shown, the end bodies 200, 500 have irregular kidney shapes, but other irregular and regular shapes are contemplated. First end body 200 includes an upper or first end body section 202 joined to a lower or second end body section 204. An end body gap 206 is between the first and second end body sections 202, 204. Two joint pin holes 208, 210 each extend through the first and second end body sections 202, 204. The upper exterior surface of the first end body 200 is a first bone engagement surface 214, which may be superiorly oriented. The lower exterior surface of the second end body section 204 is a second bone engagement surface 216, which may be inferiorly oriented. One or more bone engagement features such as teeth 220 may project from the bone engagement surfaces 214, 216. In other embodiments, bone engagement features may include teeth, spikes, pins, posts, points, surface roughening, bosses, ridges, or keels, among others. The size and/or distribution of the bone engagement features may vary.

First end body section 202 is circumscribed by a first end body section periphery 203, which may be smooth and include rounded curves. Similarly, second end body section 204 is circumscribed by a second end body section periphery 205, which may be smooth and include rounded curves. The smooth surface and rounded curves may promote smooth articulation with intermediate bodies of the implant.

First end body 200 includes a shaft retainer 222, which may include opposed grooves formed into first and second end body sections 202, 204, opening into end body gap 206. Shaft retainer 222 includes a shaft opening 224 flanked by shoulders 226, 228. A shaft pin hole 230 extends through the first end body section and opens into the shaft opening 224. A shaft retention pin 184 is shaped to be received in shaft pin hole 230 to retain a portion of shaft 110 in the shaft retainer 222 so that the shaft is rotatable about its center longitudinal axis, and otherwise fixed to the first end body 200.

Second end body 500 includes an upper or first end body section 502 joined to a lower or second end body section 504. An end body gap 506 is between the first and second end body sections 502, 504. Two joint pin holes 508, 510 each extend through the first and second end body sections 502, 504. The upper exterior surface of the second end body 500 is a first bone engagement surface 514, which may be superiorly oriented. The lower exterior surface of the second end body section 504 is a second bone engagement surface 516, which may be inferiorly oriented. One or more bone engagement features such as teeth 220 may project from the bone engagement surfaces 514, 516. In other embodiments, bone engagement features may include teeth, spikes, pins, posts, points, ridges, grooves, surface roughening, bosses, or keels, among others. The size and/or distribution of the bone engagement features may vary.

First end body section 502 is circumscribed by a first end body section periphery 503, which may be smooth and include rounded curves. Similarly, second end body section 504 is circumscribed by a second end body section periphery 505, which may be smooth and include rounded curves. The smooth surface and rounded curves may promote smooth articulation with intermediate bodies of the implant.

Second end body 500 includes a shaft retainer 522, which may include opposed grooves formed into first and second end body sections 502, 504, opening into end body gap 506. A shaft pin hole 530 extends through the first and second end body sections 502, 504 and. A shaft retention pin 198 is shaped to be received in shaft pin hole 530 to retain a portion of shaft 110 in the shaft retainer 522 so that the shaft is fixed to the second end body 500.

The implant 100 may be moved or transformed between the closed and expanded configurations by means of a two-piece adjustment mechanism. Shaft 110 includes a male half 800 and a female half 900. The male half 800 includes a socket 802. In the illustrated example, the male half 800, or screw, is placed through the first end body 200, into the shaft retainer 222 and is held captive to the end body 200 by a shoulder-to-shoulder thrust surface contact and pin 184 in shaft pin hole 230 to retain the screw 800 in the implant 100. The female half 900, or socket, is placed through the second end body 500 into shaft retainer 522 and is retained in place by means of a cross pin 198. A portion of screw 800 is threadably received in socket 900. In this arrangement, turning the screw 800 relative to the socket 900 causes the end bodies 200, 500 to move closer together or farther apart. The screw 800 and socket 900, forming shaft 110, may be said to establish a central longitudinal axis 105 of the device 100. The engagement length between the two screw halves 800, 900 may be maximized because the mechanism has a secondary function of maintaining proper alignment between the first and second end bodies 200, 500 along the central longitudinal axis of the implant 100. In alternate embodiments, shaft 110 may be a jackscrew, telescoping member, turnbuckle, ratchet, or other variable length coupling.

A first intermediate body 120 and a second intermediate body 130 are each disposed at least partially between, or intermediate, the first and second end bodies 200, 500. The intermediate bodies are movably joined to the end bodies, allowing the expansion in the width of the implant. First intermediate body 120 includes two subunits, a first arm 300 and a second arm 400. First arm 300 is movably connected to first end body 200 at a joint 150, and to second arm 400 at a joint 152. Second arm 400 is movably connected to second end body 500 at joint 154. First arm 300 includes a tab 302 and a slot 304. Two pin holes 306, 308 extend through tab 302 and slot 304, respectively. Bone-contacting surfaces 310, 312 are formed on opposing sides of the first arm 300. Second arm 400 includes two tabs 402, 404 with pin holes 406, 408. Bone-contacting surfaces 410, 412 are formed on opposing sides of the second arm 400.

Second intermediate body 130 includes two subunits, a third arm 600 and a fourth arm 700. Third arm 600 is movably joined to first end body 200 and fourth arm 700 at joints 160, 158, and fourth arm 700 is movably joined to second end body 500 and third arm 600 at joints 156, 158. Third arm 600 includes a tab 602 and a slot 604. Two pin holes 606, 608 extend through tab 602 and slot 604, respectively. Bone-contacting surfaces 610, 612 are formed on opposing sides of the third arm 600. Fourth arm 700 includes two tabs 702, 704 with pin holes 706, 708. Bone-contacting surfaces 710, 712 are formed on opposing sides of the fourth arm 700. Any of the bone-contacting surfaces may include one or more bone engagement features as described previously. In other embodiments bodies 200, 500 and arms 300, 400, 600, 700 may be bodies, arms, beams, links, wall elements, units, subunits, spacers, or plates, among other suitable members.

Figure 3:
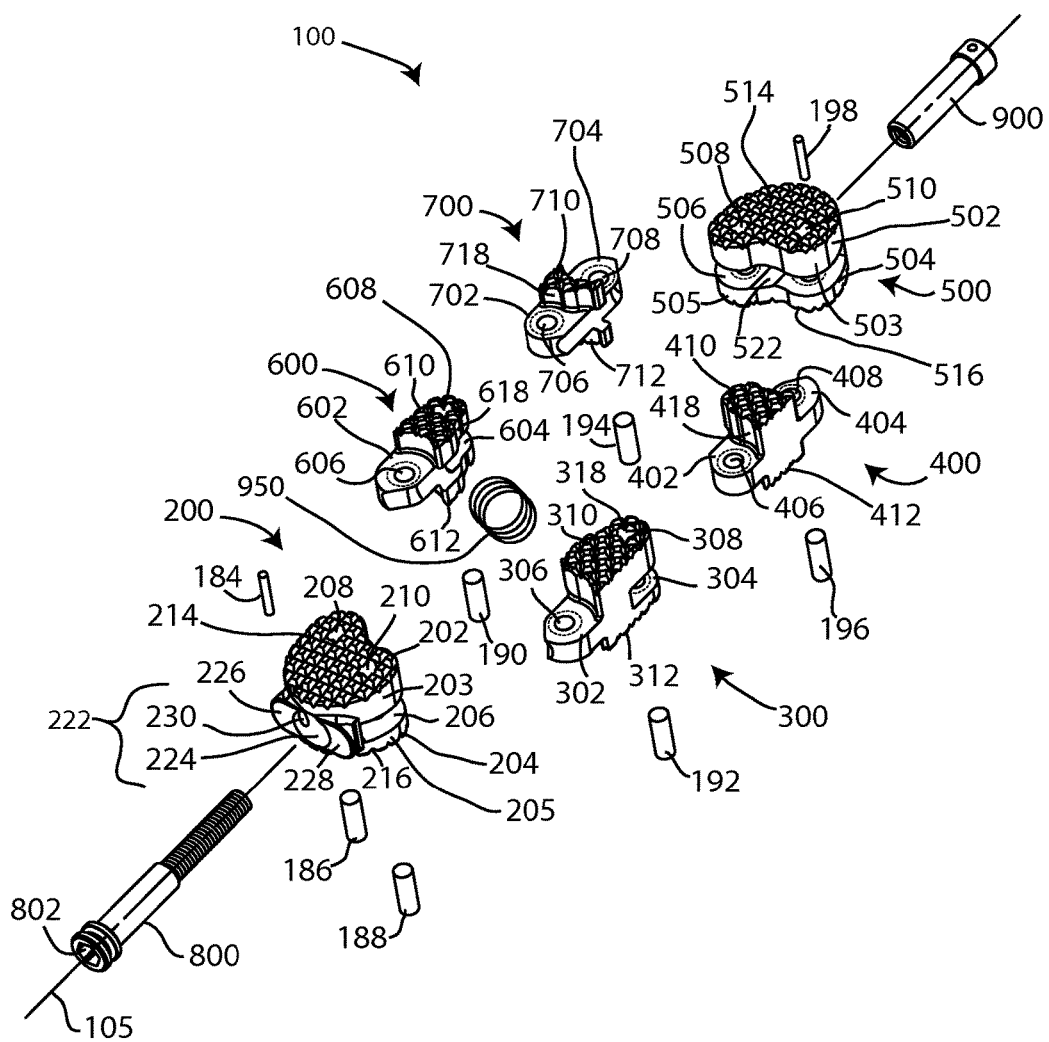
FIG. 3 is an exploded perspective view of the fusion device of FIG. 1.

The joints between the end bodies and arms, and between the arms, may be hinge type connections. Each joint 150, 152, 154, 156, 158, 160 may include a pin extending through at least two pin holes. Implant material immediately surrounding each pin hole may be referred to as joint housing. Referring to FIG. 3, the joint housing around selected pin holes is indicated by the area within the dashed line encircling the pin holes, and represents the minimum material needed to support the joint and permit it to function, allowing pivoting of the respective end bodies or arms about the pin. Material outside the dashed lines may be referred to as auxiliary housing, and represents material in excess of the minimum needed, the auxiliary housing functioning to reinforce and strengthen the joint housing, and stabilize the implant across the transverse plane of the implant. The additional structure provided by the auxiliary housing may prevent flexing of the implant 100 across the transverse plane of the implant. Each of the joints of implant 100 includes joint housing and auxiliary housing.

Arms 300, 400, 600 and 700 are each irregularly shaped. The total bone-contacting surface area of first intermediate body 120, which includes bone-contacting surfaces 310, 410 on one side and bone-contacting surfaces 312, 412 on the opposing side, is greater than the total bone contacting surface area of the second intermediate body 130. Where each end body 200, 500 interfaces with each intermediate body 120, 130, there is an elongated gap 140, or clearance between the periphery of the end body and the adjacent intermediate body. As may be seen in FIGS. 4 and 5, whether implant 100 is expanded or compact, the width of the elongated gap between the opposing peripheral surfaces of the end bodies and the intermediate bodies remains substantially constant. This is in contrast to, for example, a door or piano type hinge in which the gap between the opposing surfaces widens as the door is opened, forming a V shape.

Pins 186, 188, 190, 192, 194, and 196 each form a pivot point, or pivot axis about which the end bodies and intermediate bodies pivot to transform the implant 100 between the compact and expanded configurations. Pin 188 extends through pin holes 210 and 306 to pivotably connect, or hinge end body 200 to first arm 300 at joint 150. Pin 192 extends through pin holes 308 and 406 to pivotably connect, or hinge first arm 300 to second arm 400 at joint 152. Pin 196 extends through pin holes 510 and 408 to pivotably connect, or hinge second arm 400 to second end body 500 at joint 154. Pin 194 extends through pin holes 508 and 708 to pivotably connect, or hinge second end body 500 to fourth arm 700 at joint 156. Pin 194 extends through pin holes 608 and 706 to pivotably connect, or hinge fourth arm 700 to third arm 600 at joint 158. Pin 186 extends through pin holes 208 and 606 to pivotably connect, or hinge third arm 600 to end body 200 at joint 160. These pivotable joints allow the expansion and contraction of the implant 100. The pivoting movement of the arms during expansion or contraction may be referred to as scissor-jack movement. It is appreciated that in other embodiments, more arms or subunits could be included with suitable pivotable connections or joints. One example includes a lattice type construction with multiple arms interconnected with pivotable connections. It is also appreciated that in other embodiments, the end bodies may be pivotably connected to each other.

Figure 5:
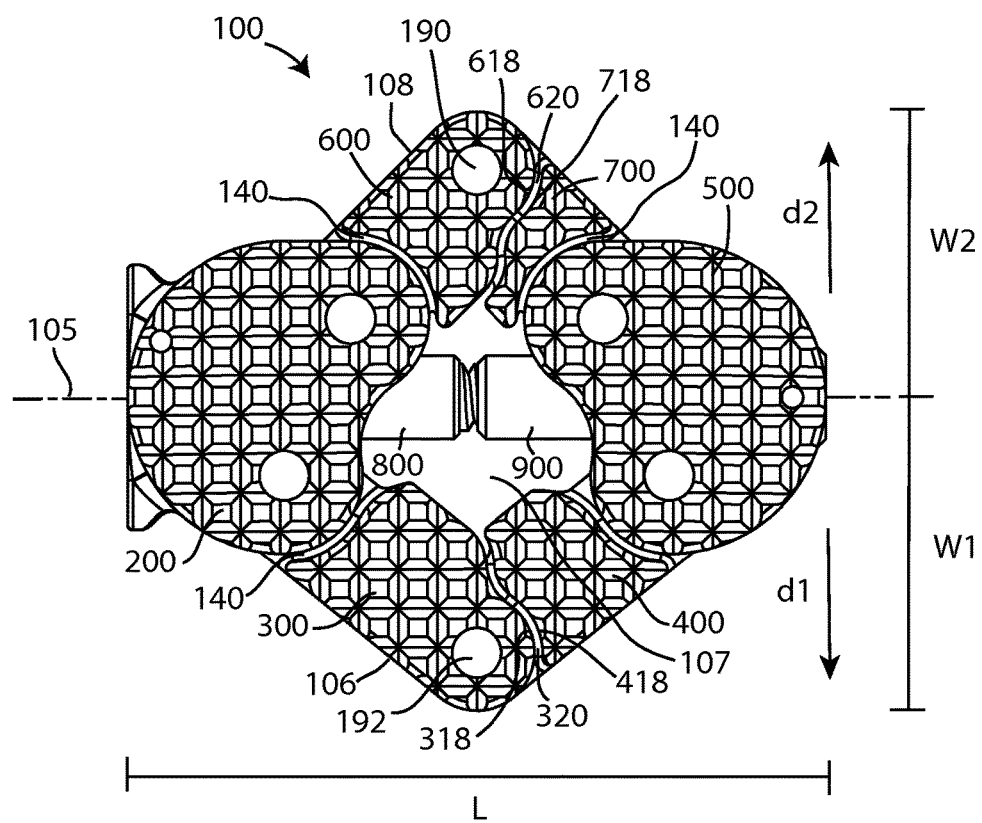
FIG. 5 is a top view of the fusion device of FIG. 2.

Referring to FIGS. 3-5, arm 300 interfaces with arm 400 at a first interface 320, and arm 600 interfaces with arm 700 at a second interface 620. The interfaces 320, 620 limit the transformation of the implant into the expanded configuration and prevent over-expansion of the implant. Arm 400 includes an articulation surface 418, arm 300 includes an articulation surface 318, arm 600 includes an articulation surface 618, and arm 700 includes an articulation surface 718. The articulation surfaces may include curves, and may be complexly curved. Articulation surfaces 418, 718 may provide stops to expansion of implant 100 beyond a selected limit. For example, as seen in FIG. 5 once the articulation surface 718 of arm 700 fully encounters an opposing articulation surface 618 of arm 600, the interface 620 limits any further movement of 600 and 700 relative to one another in that direction. Similarly, articulation surfaces 318, 418 may cooperate in the expanded configuration to prevent further expansion of the implant.

Referring to FIGS. 4 and 5, implant 100 has an implant length L and an implant width W. The implant length may be defined by the length of the shaft 110 along a longitudinal axis 112, and may vary between the compact configuration and the expanded configuration. In the examples shown, length L is longest in the compact configuration and shortest in the expanded configuration. The implant width W is measured at the widest point crossing the implant from one outer edge of the implant across one or more of the bodies 200, 300, 400, 500, 600, 700, to an opposite outer edge of the implant, measured perpendicular to the longitudinal axis 112 of the shaft 110. In the examples shown, width W is narrowest in the compact configuration and widest in the expanded configuration. The width W may have a first segment $W_1$ measured in a first direction d1 perpendicular to the implant length, and a second segment $W_2$ measured in a second direction d2 perpendicular to the implant length and opposite the first direction, wherein $W=W_1+W_2$. As implant 100 is transformed from the compact configuration to the expanded configuration, the increase in the first width segment, along the first direction, may be greater than the increase in the second width segment, along the second direction. This may be called asymmetric expansion. Asymmetric expansion may be advantageous when using a lateral surgical approach. A true lateral approach requires passing through the psoas muscle to reach the intervertebral disc space. In order to minimize trauma to the muscle and the nerves in its vicinity, it may be preferable to shift the lateral trajectory anteriorly to access the anterior third of the disc space. An implant that expands more in the posterior direction than in the anterior direction may more effectively fill the disc space, resulting in a more stable final construct. In the example shown and described, the first direction d1 may be posterior and the second direction may be anterior d2.

Figure 6A:
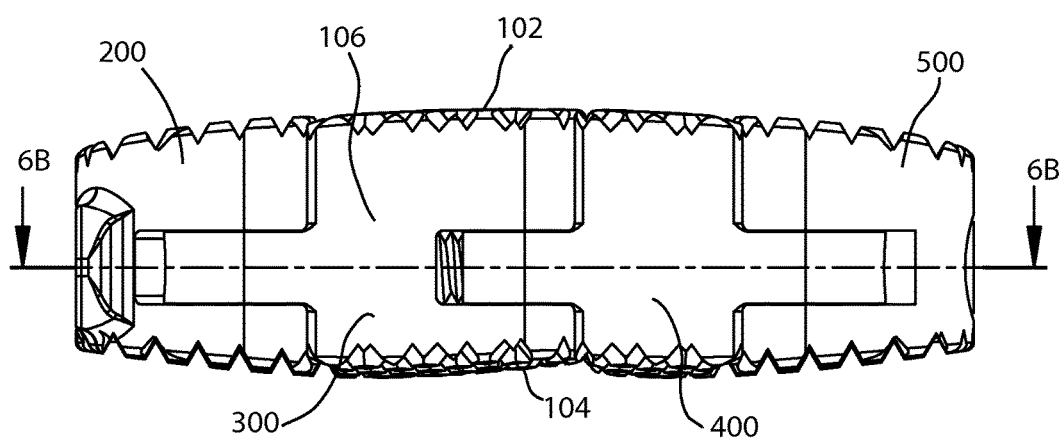
FIG. 6A is a side view of the fusion device of FIG. 1.
Figure 6B:
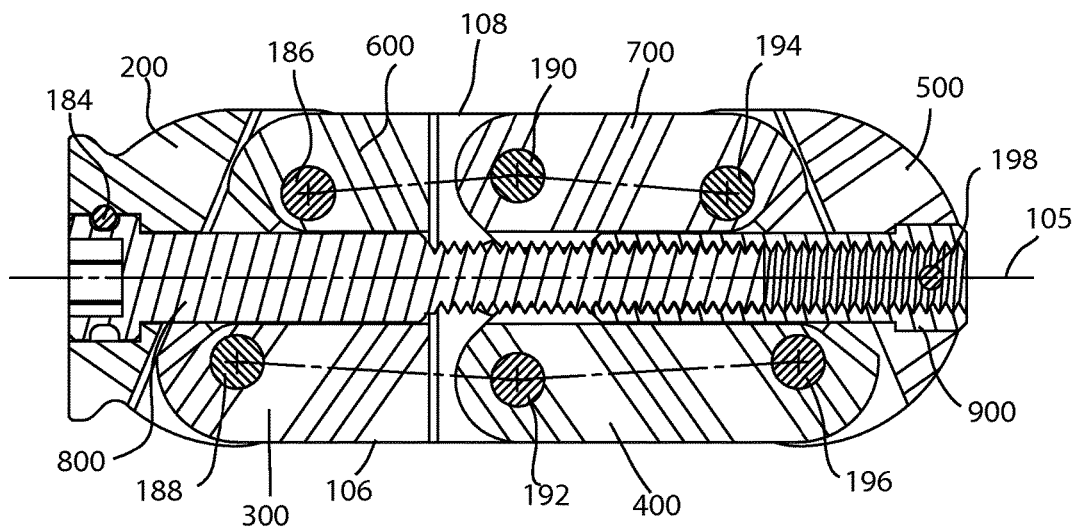
FIG. 6B is a cross section view of the fusion device of FIG. 1 taken along section line 6B-6B shown in FIG. 6A.
Figure 7A:
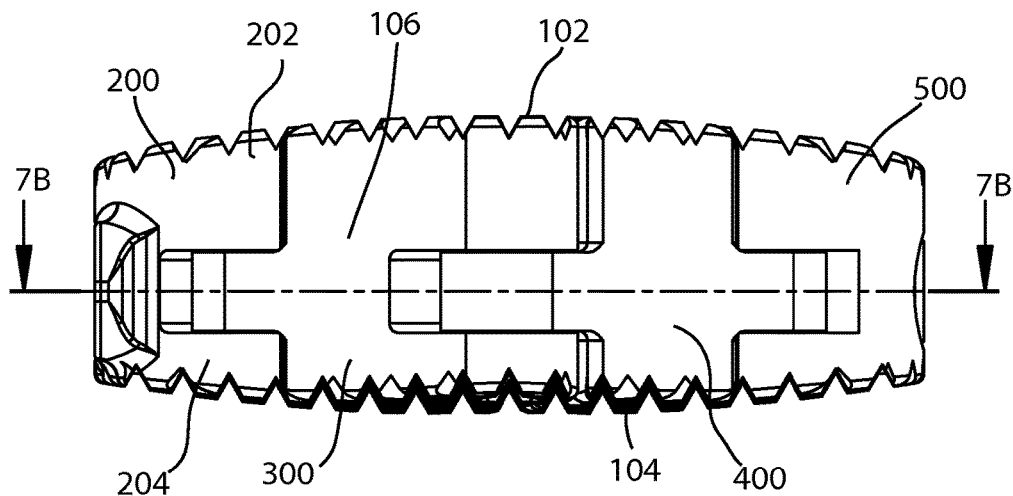
FIG. 7A is a side view of the fusion device of FIG. 2.
Figure 7B:
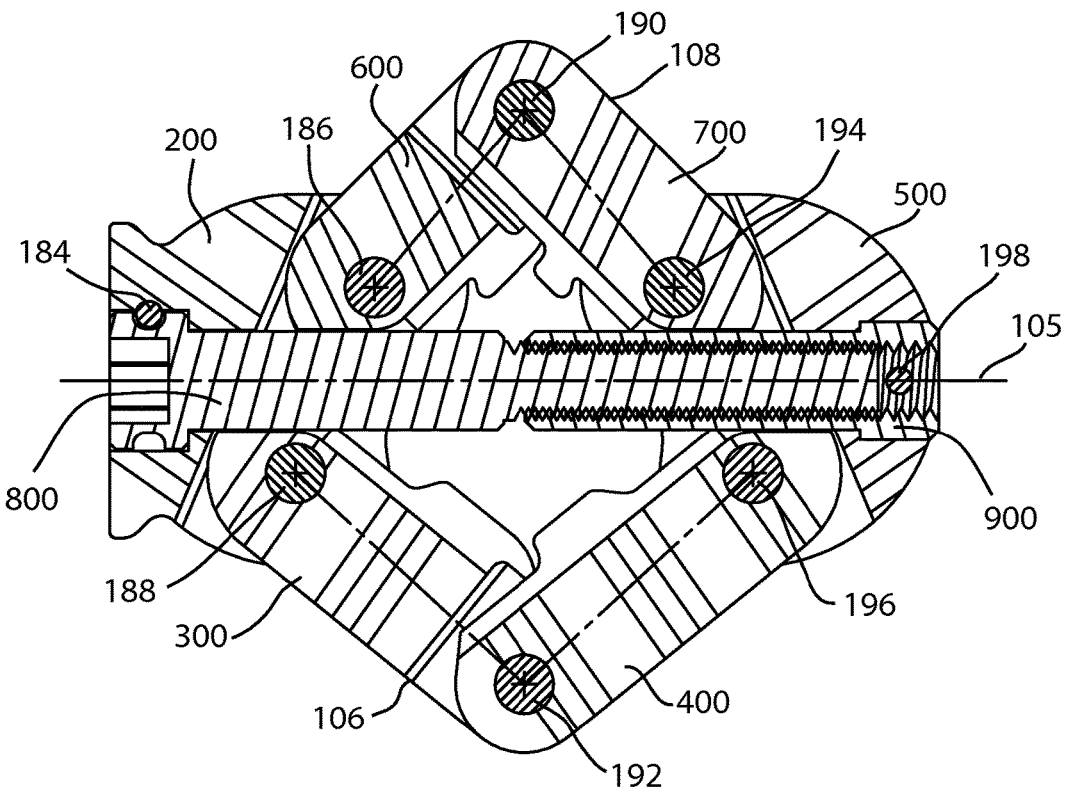
FIG. 7B is a cross section view of the fusion device of FIG. 2 taken along section line 7B-7B shown in FIG. 7A.

FIGS. 6A-7B further illustrate the compact and expanded configurations of implant 100. FIG. 6A is a side view of implant 100 in the compact configuration, and FIG. 6B is a cross-sectional view taken along line B-B in FIG. 6A. FIG. 7A is a side view of implant 100 in the expanded configuration, and FIG. 7B is a cross-sectional view taken along line B-B in FIG. 7A.

The compact configuration may also be described as a closed configuration, a reduced size configuration, an initial configuration, or an insertion configuration. Referring to FIGS. 1, 4, 6A-B, and 9B, in the closed configuration, the bodies 200 and 500 are positioned so that the bodies 300, 400, 600, and 700 extend more or less straight between the bodies 200, 500. In this arrangement, the device 100 has a relatively small profile or cross sectional area perpendicular to the center longitudinal axis 105 of the device 100. It can be appreciated that pin 190 is displaced farther away from the center longitudinal axis than pins 186 and 194, and pin 192 is displaced farther away from the center longitudinal axis than pins 188 and 196, even in the closed configuration. This arrangement may facilitate transforming the implant to the expanded configuration.

The expanded configuration may also be described as a larger size configuration, a final configuration, or an implanted configuration. Referring to FIGS. 2, 5, 7B, and 8B, in the expanded configuration, the bodies 200 and 500 are positioned so that the bodies 300, 400, 600, and 700 are angled outwardly from the center longitudinal axis of the device 100. More specifically, in the expanded configuration, pins 190, 192 are displaced farther away from the center longitudinal axis 105 than their respective positions in the closed configuration. In use, the device 100 may be inserted into an intervertebral disc space so that expansion takes place in the transverse plane, or in a plane parallel to one of the vertebral endplates defining the intervertebral disc space, or in a plane parallel to the plane that is equidistant from these vertebral endplates. In this arrangement, the expanded configuration increases the effective contact area between the device 100 and the vertebral endplates. The size of the implant window 107 may also be increased in the expanded configuration.

Figure 8A:
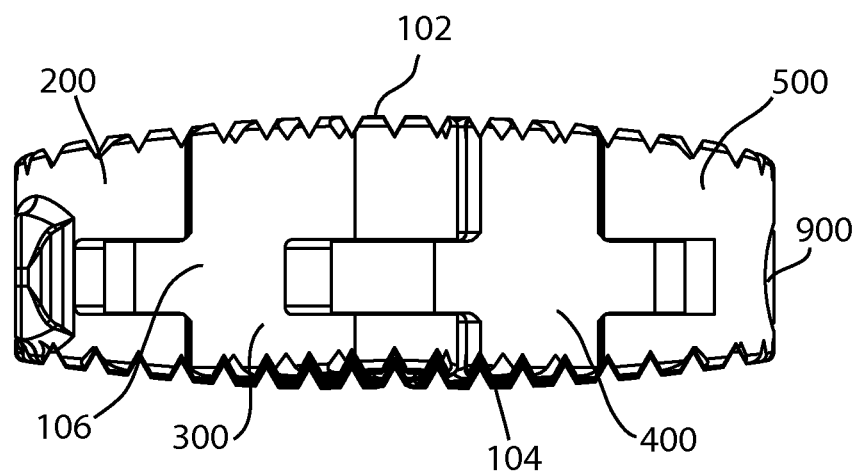
FIG. 8A is a side view of the fusion device of FIG. 2.
Figure 8B:
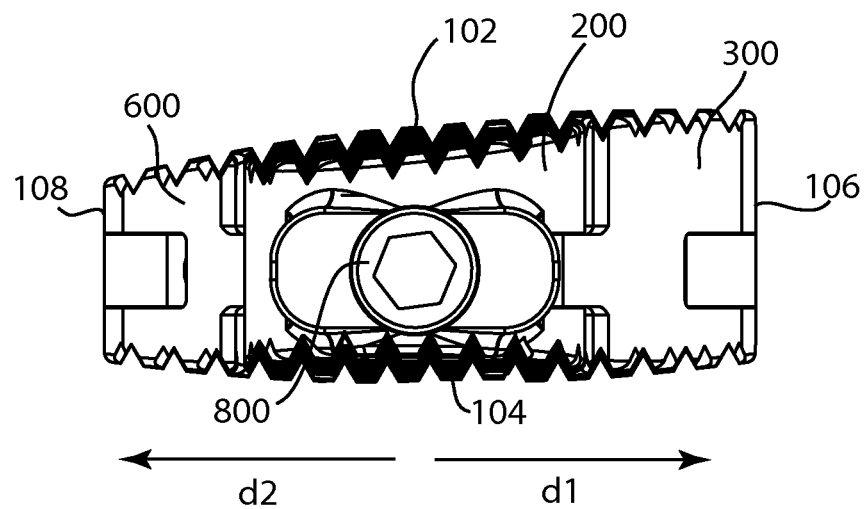
FIG. 8B is an end view of the fusion device of FIG. 2.
Figure 9A:
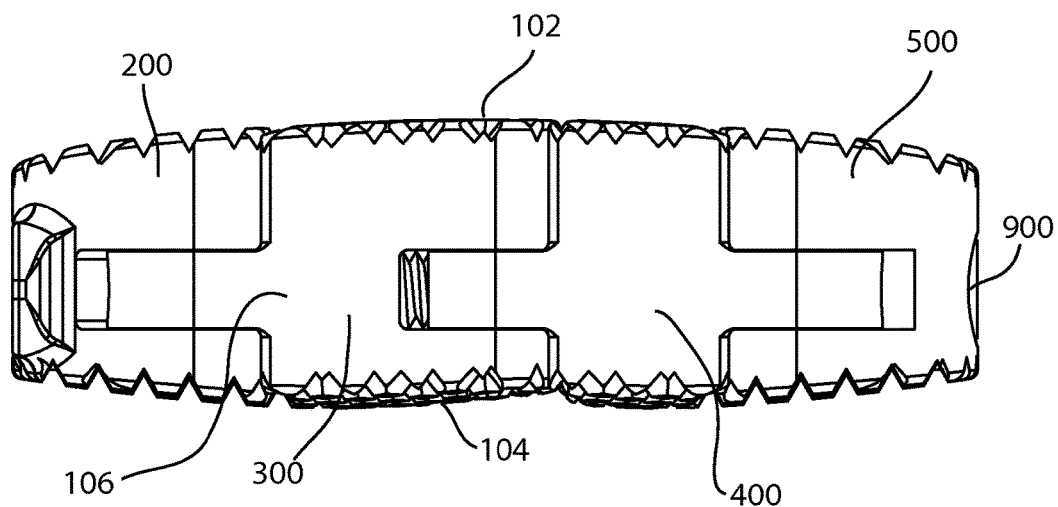
FIG. 9A is a side view of the fusion device of FIG. 1.
Figure 9B:
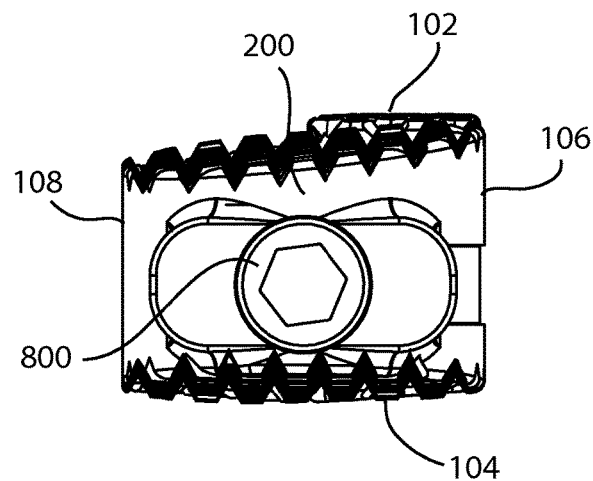
FIG. 9B is an end view of the fusion device of FIG. 1.

It is frequently desirable to use an implant that includes a lordotic angle that matches the patient's natural spinal curvature. The disclosed implant 100 includes a lordotic curvature that is consistent or congruent across all the implant bodies 200, 300, 400, 500, 600, and 700 when the implant 100 is in the expanded position, as may be seen in FIGS. 8A-B. As a consequence, the bone-contacting surfaces 102, 104 may not be consistent when the implant is in the insertion or compact configuration, as shown in FIGS. 9A-B.

The height of the implant may be measured as the distance between the first and second bone-contacting surfaces 102, 104. The height maybe measured at first edge 106, second edge 108, or between the first and second edges and generally perpendicular to the second bone-contacting surface 104. As seen in FIG. 8B, the implant height measured along first direction d1, toward the first side 106 is greater than the implant height measured along the second direction d2, toward the second side 108. The asymmetric expansion of implant 100 is also visible in FIG. 8B. In the example shown, when implant 100 is inserted into the disc space between two vertebral bodies and expanded as described herein with direction d1 pointing posteriorly, the implant 100 will provide a lordotic correction, as the implant increases in height from the anteriorly oriented second edge 108 to the posteriorly oriented first edge 106. In alternative embodiments the implant may provide a kyphotic or scoliotic correction, by being implanted in a different orientation and/or by forming the implant with the height differential toward a different edge or end of the implant.

FIGS. 10A-12B show an example of an inserter instrument, or tool, for the expanding fusion device. The inserter 1000 includes a handle portion 1002, a shaft portion 1004 and a working end 1006. Working end 1006 includes a pair of opposing first and second jaws 1010, 1012 which may clamp onto the implant 100. Other styles of clamps or connections can be envisioned to achieve the same outcome. The inserter 1000 may also include a drive tip 1020 which engages the screw 800 to transmit torque to move the implant 100 between the compact and expanded configurations. The width of the shaft portion 1004 is about equal to the width of the implant 100 in the compact configuration. This allows the implant and inserter shaft to pass through a minimal sized cannula during an insertion or removal process.

Figures 10A, 10B:
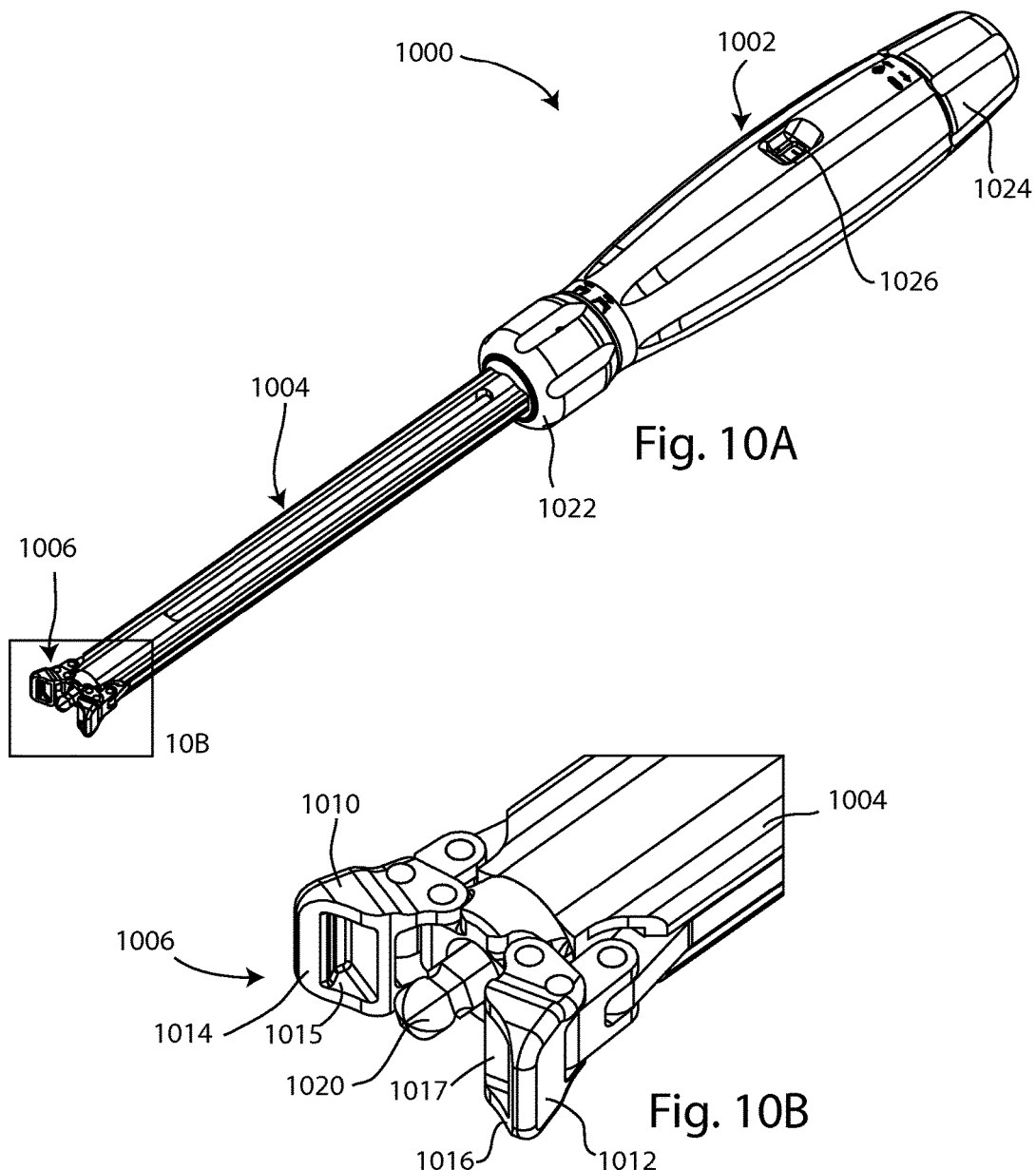
FIG. 10A is a perspective view of an inserter instrument, with jaws of the instrument in an open configuration.
FIG. 10B is an enlarged detail view of a portion of the instrument of FIG. 10A.
Figure 11A:
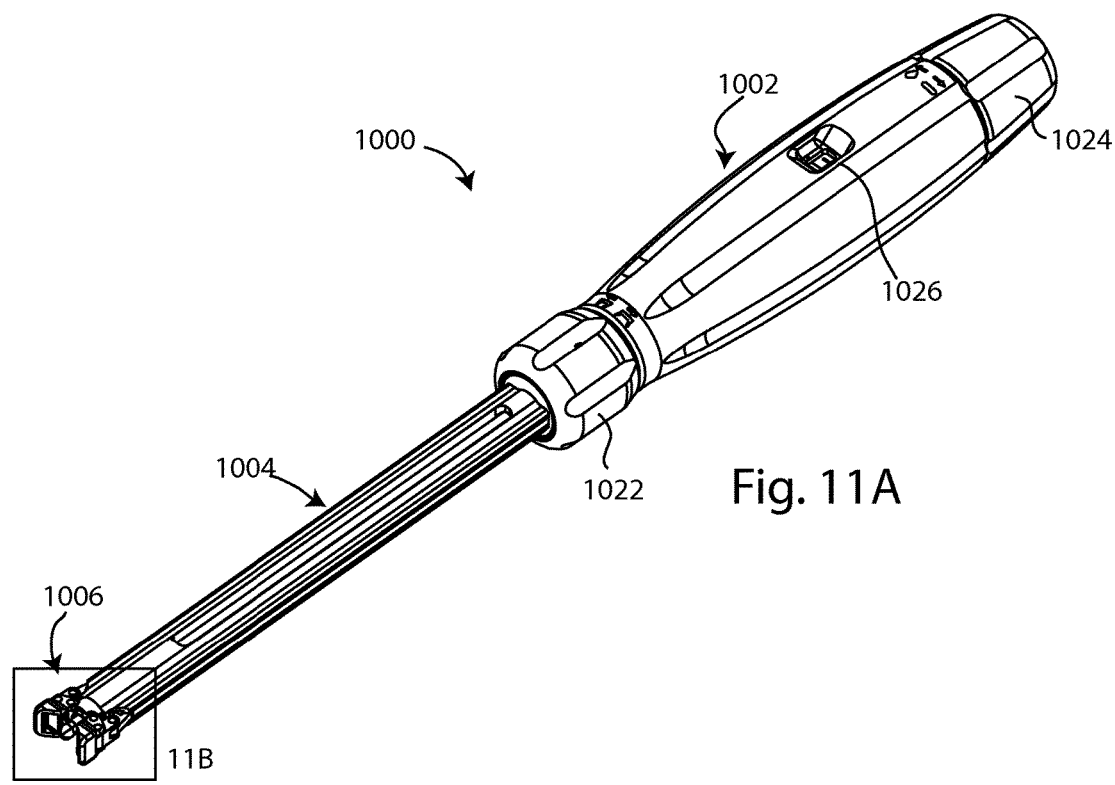
FIG. 11A is a perspective view of an inserter instrument of FIG. 10A with the jaws in a closed configuration.
Figure 11B:
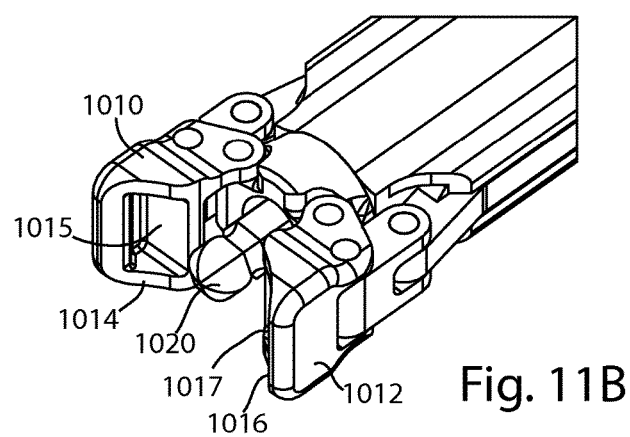
FIG. 11B is an enlarged detail view of a portion of the instrument of FIG. 11A.
Figure 12A:
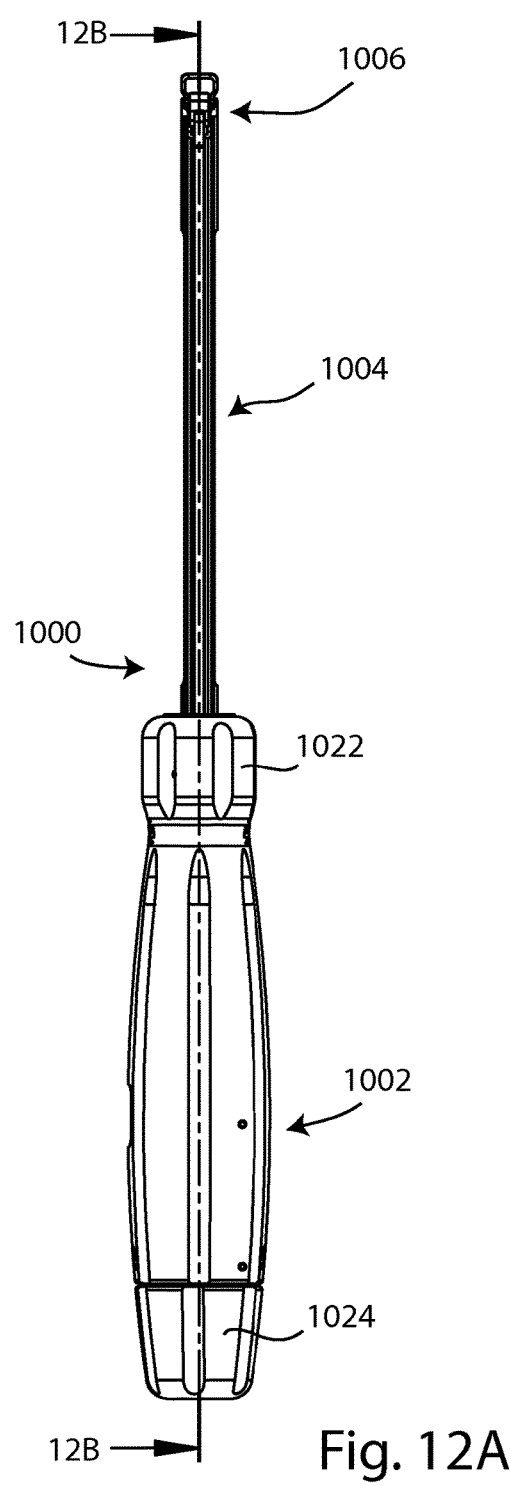
FIG. 12A is a side view of the instrument of FIG. 10A.
Figure 12B:
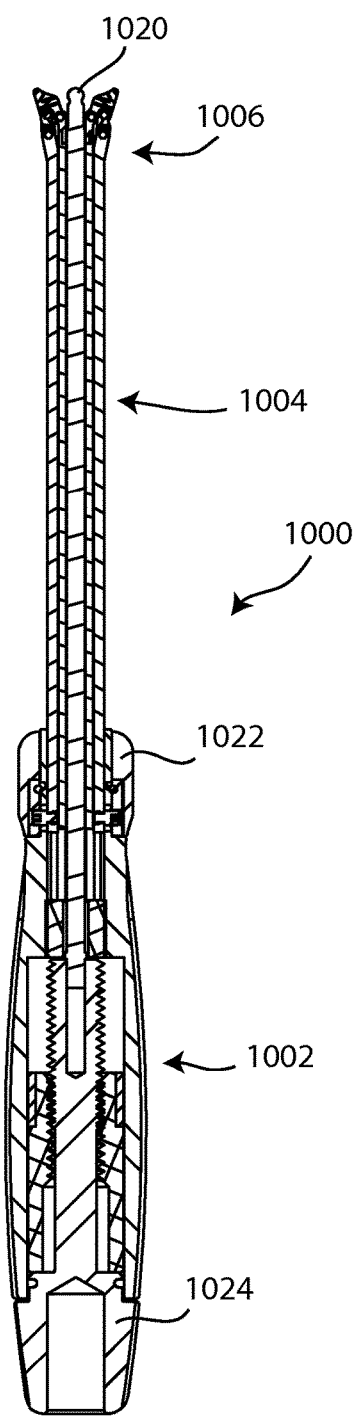
FIG. 12B is a cross section view of the instrument of FIG. 10A taken along section line 12B-12B shown in FIG. 12A.

Referring to FIGS. 10B and 11B, enlarged views of working end 1006 show details of the jaws 1010, 1012 and drive tip 1020. First jaw 1010 includes a clamping surface 1014 and a recess 1015, and opposing second jaw 1012 similarly includes a clamping surface 1016 and a recess 1017. The drive tip 1020 may be shaped to complementarily engage with screw socket 802. Moving and locking the jaws may be accomplished via actuation of a control mechanism on the inserter 1000. For example a first knob 1022 of the handle 1002 may be rotated to move, lock or unlock the jaws. In other embodiments a lever, button or tab may be actuated to move, lock or unlock the jaws. Another control mechanism on the inserter 1000 may be actuated to drive the drive tip 1020. For example, a second knob 1024 on the handle portion 1002 may be rotatable to rotate the tip 1020. An indicator 1026 may be present on the inserter 1000 to indicate the degree of actuation of tip 1020, so the surgeon can tell to what degree the implant has been expanded.

Figure 13:
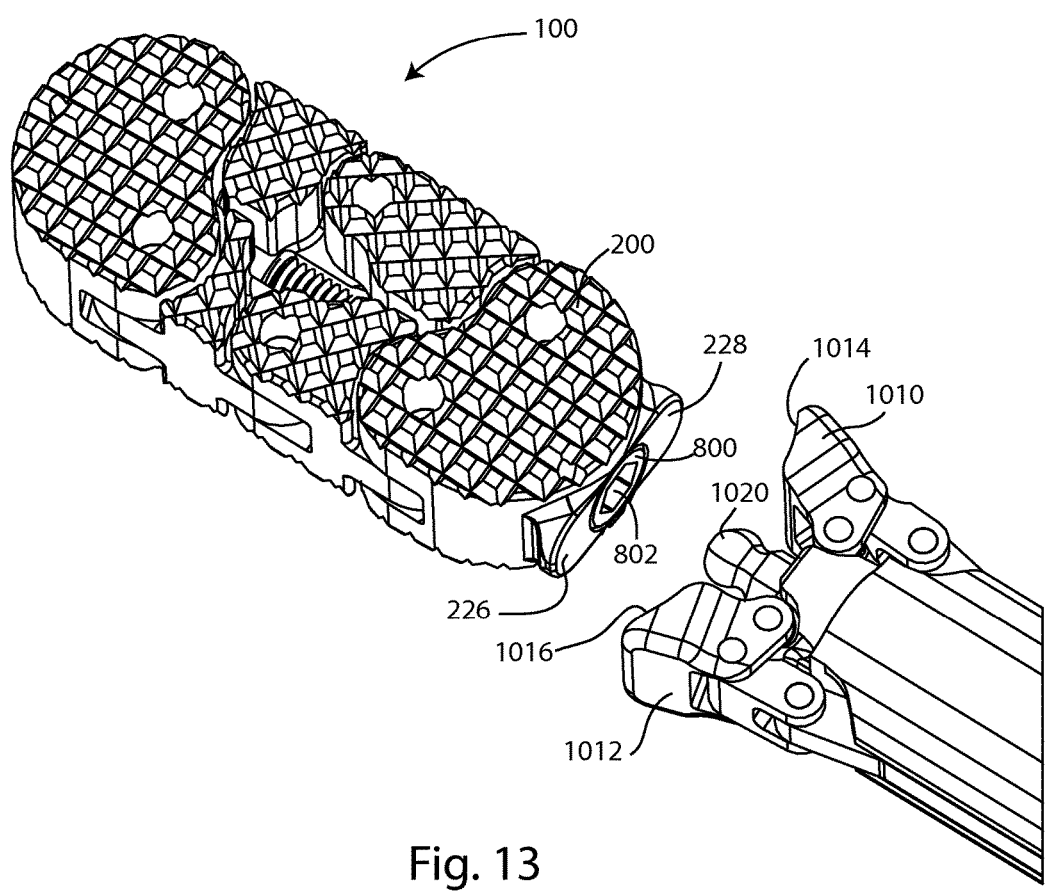
FIG. 13 is an enlarged detail view of the fusion device of FIG. 1 and a portion of the instrument of FIG. 10A.
Figure 14:
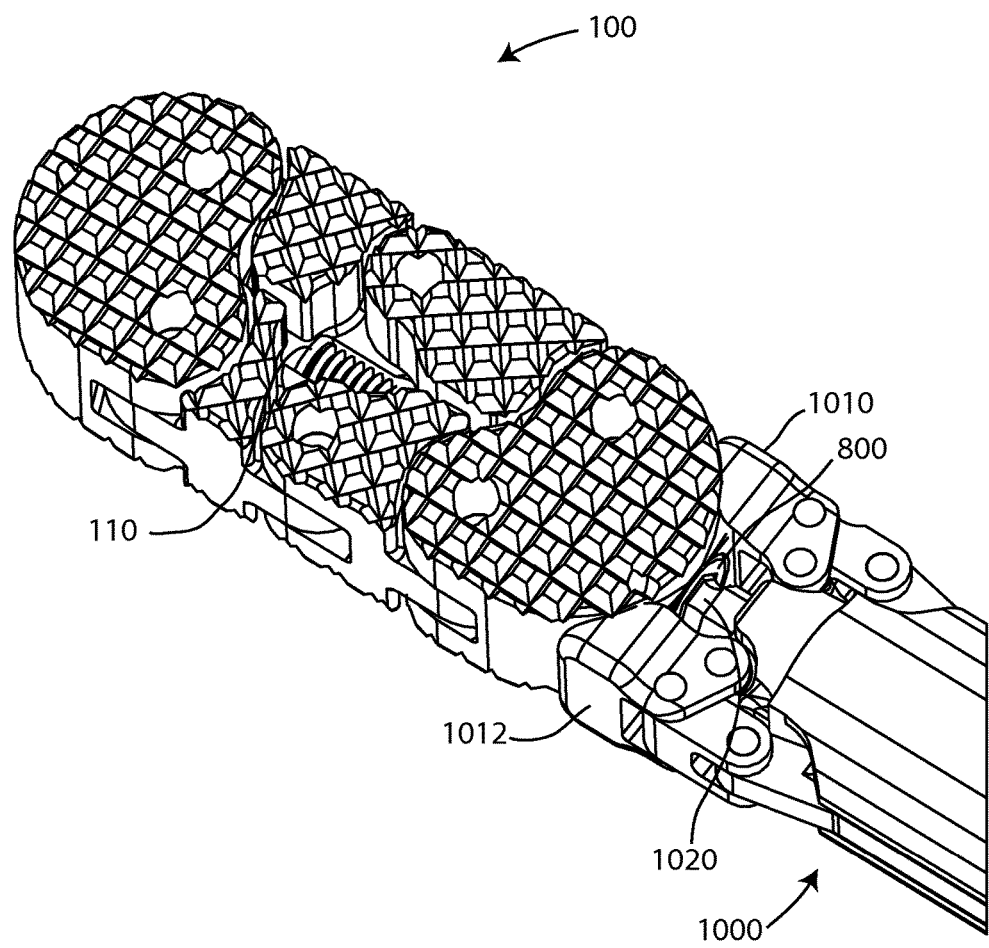
FIG. 14 is an enlarged detail view of the fusion device and instrument portion of FIG. 13 coupled together, the implant in the compact configuration.
Figure 15:
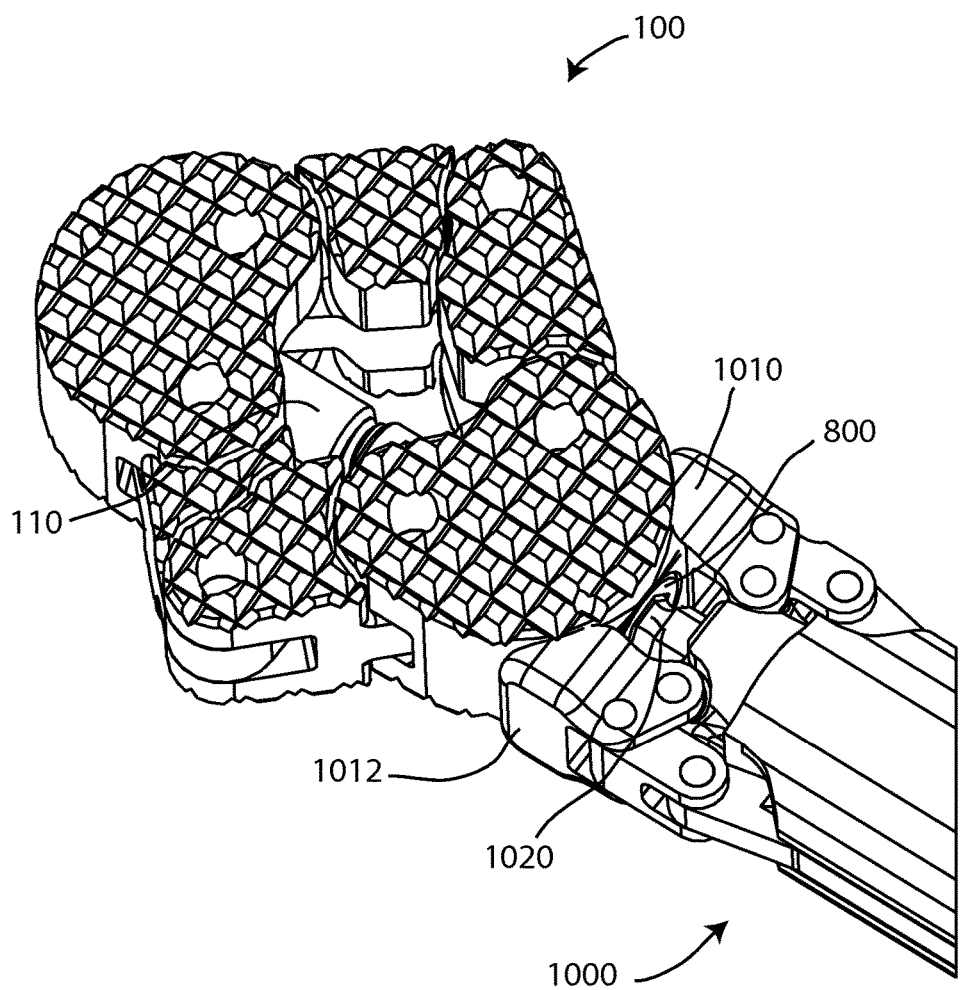
FIG. 15 is an enlarged detail view of the fusion device and instrument portion of FIG. 13 coupled together, the implant in the expanded configuration.

In use, handle portion 1002 of inserter 1000 may be actuated to open jaws 1010, 1012 into the open position seen in FIGS. 10A and 10B. Referring to FIGS. 13 and 14, the implant 100 may be mounted on the inserter 1000 with drive tip 1020 coaxially received in screw socket 802. Clamping surfaces 1014, 1016 abut end body 200 with shoulders 226, 228 received in recesses 1017, 1015. The interface between the shoulders and recesses may be a dovetail interface or other undercut interface. Once the implant 100 is mounted on the inserter, the jaws 1010, 1012 may be moved to the closed position seen in FIGS. 11A, 11B and 14, and may be locked in the closed position. In this arrangement, with implant 100 in the compact configuration and mounted on inserter 1000, the implant 100 may be inserted, or implanted, into an intervertebral space between the endplates of two adjacent vertebral bodies. The implantation may be along a lateral approach into the anterior third of the intervertebral space. After insertion of the compact implant to the intervertebral space, drive tip 1020 may be actuated, or rotated to turn screw 800. As set forth above, actuation of screw 800 may shorten shaft 110 and simultaneously expand the width of the implant, as arms 300, 400, 600, 700 are urged outward. The expansion may be asymmetrical, with the implant 100 expanding further toward the posterior direction.

Variations of the implant 100 are contemplated. For example, the implant 100 may be provided with different overall heights covering a range of intervertebral disc heights. In other examples, the implant 100 may be provided with different lordotic and/or kyphotic angles. In still other examples, the implant 100 may be provided with other patterns or features, such as spikes, keels, or the like on the bone contacting surfaces that provide stability and/or resistance to shifting positions. The implant may be made from metal, polymer, ceramic, composite, or other biocompatible and sterilizable material. Different materials may be combined in what is described herein as a single part.

The screw 800 and/or socket 900 may be fenestrated so that bone graft, marrow, or other therapeutic or structural material may be introduced into the expanded implant center, or implant window 107.

In an embodiment, one or more springs may be included in the implant to provide spring bias to urge the implant toward the expanded configuration. For example, a spring 950 may be included between the first and second intermediate bodies 120, 130 to urge the implant toward the expanded configuration. In this arrangement, the various parts of the implant may be configured so that pin 190 is even with or closer to the center longitudinal axis 105 than pins 186 and 194, and pin 192 is even with or closer to the center longitudinal axis 105 than pins 188 and 196 in the closed configuration.

Variations of the inserter 1000 are contemplated. For example, alternate complementary implant/inserter interfaces may be provided. In other examples, alternate mechanisms may be provided to actuate the implant grasping features of the inserter 1000. The implant grasping and driving features may be provided on separate instruments.

Figure 16:
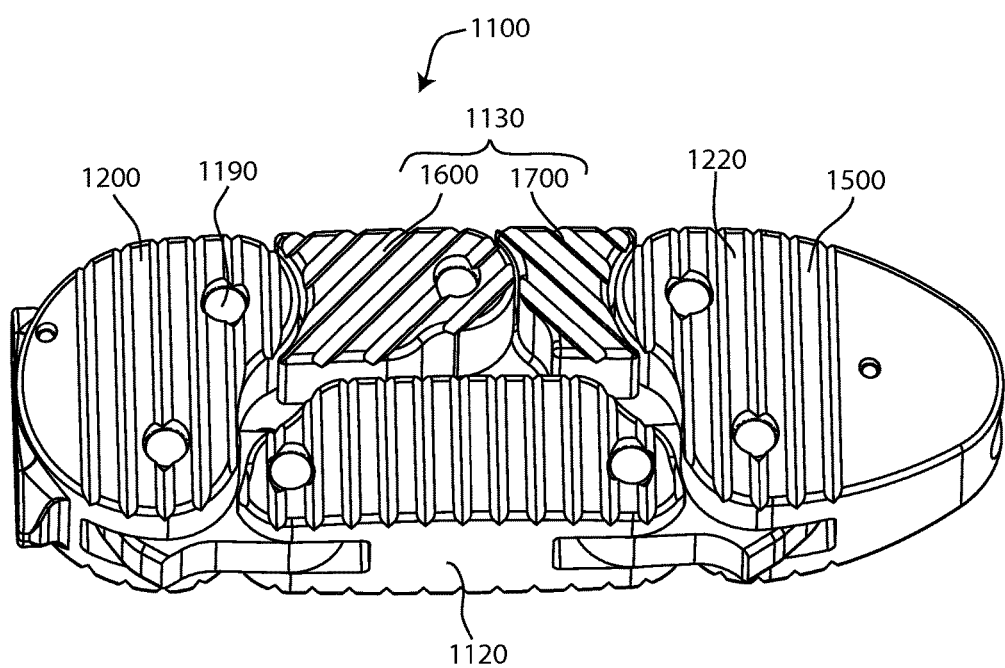
FIG. 16 is a perspective view of an alternate embodiment of an expanding fusion device, the fusion device in a compact configuration.
Figure 17:
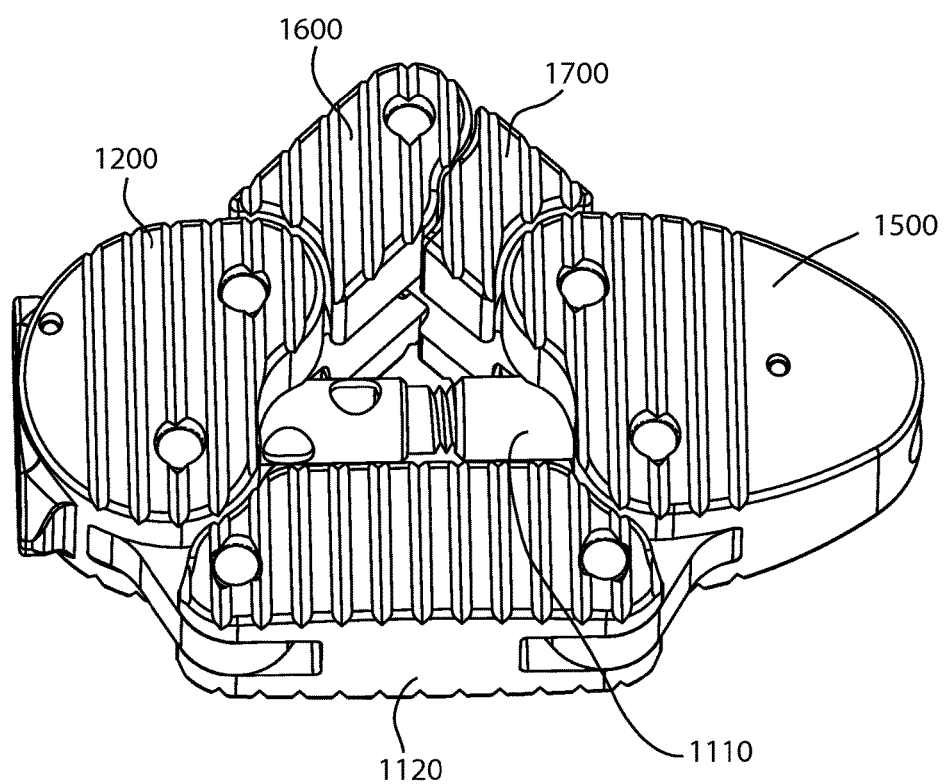
FIG. 17 is a perspective view of the fusion device of FIG. 16, the fusion device in an expanded configuration.

An alternative embodiment of an expanding fusion device, or implant, is shown in FIGS. 16 and 17. FIG. 16 shows the implant in a compact configuration and FIG. 17 shows the implant in an expanded configuration. Implant 1100 includes a central shaft 1110 joined to first and second end bodies 1200, 1500. Shaft 1110 may be fenestrated so that bone graft, marrow, or other therapeutic or structural material may be introduced into the expanded implant center, or implant window 1107. For example, two fenestrations 1109 are visible in FIG. 17. First and second intermediate bodies 1120, 1130 are disposed between the end bodies 1200, 1500. A plurality of pins 1190 connect end bodies 1200, 1500 with intermediate bodies 1120, 1130, forming joints which allow pivotal movement of the intermediate bodies relative to the end bodies. Actuation of shaft 1110 can lengthen or shorten shaft 1110 and move the implant 1100 between the compact configuration shown in FIG. 16 and the expanded configuration shown in FIG. 17, as set forth for implant 100. In the expanded configuration, the width of implant 1100 is increased, and the width increase may be greater in a first direction than in a second direction, the first and second directions perpendicular to the longitudinal axis of shaft 1110. Second intermediate body 1130 may include two arms 1600, 1700 which pivot relative to one another and to the end bodies 1200, 1500 to increase the width of the implant 1100. Bone engagement features such as ridges 1220 may be present on any bone-contacting surface of the implant. As seen in FIG. 17, the ridges 1220 may align parallel to one another in the expanded configuration of the implant 1100. The bone-contacting surface of second intermediate body 1130 may be greater than the bone-contacting surface of first intermediate body 1120. The implant 1100 may be implanted and actuated via inserter tool 1000 using methods set forth previously for implant 100. Other features set forth above in the description of implant 100 may apply to implant 1100.

Figure 18A:
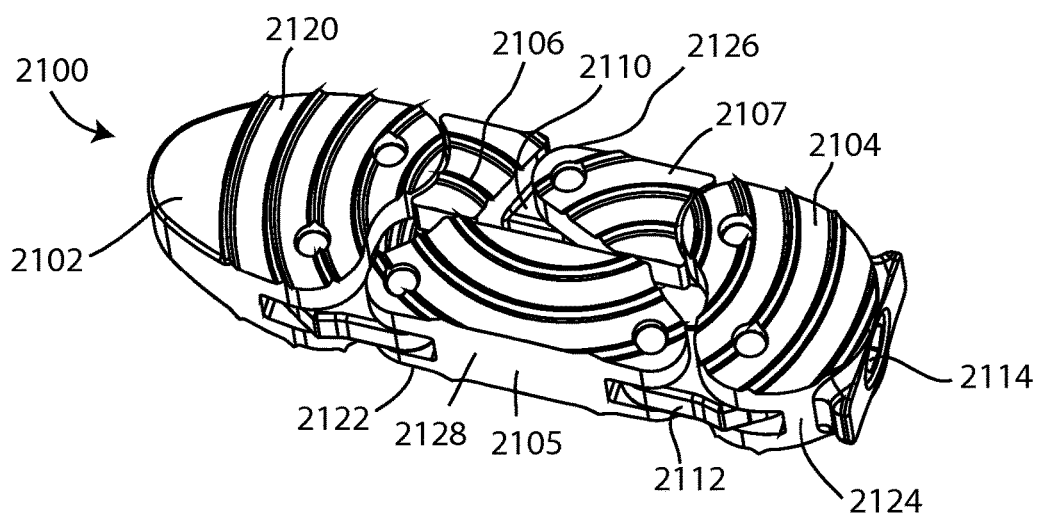
FIG. 18A is an isometric view of an expandable interbody device in a compact configuration.
Figure 18B:
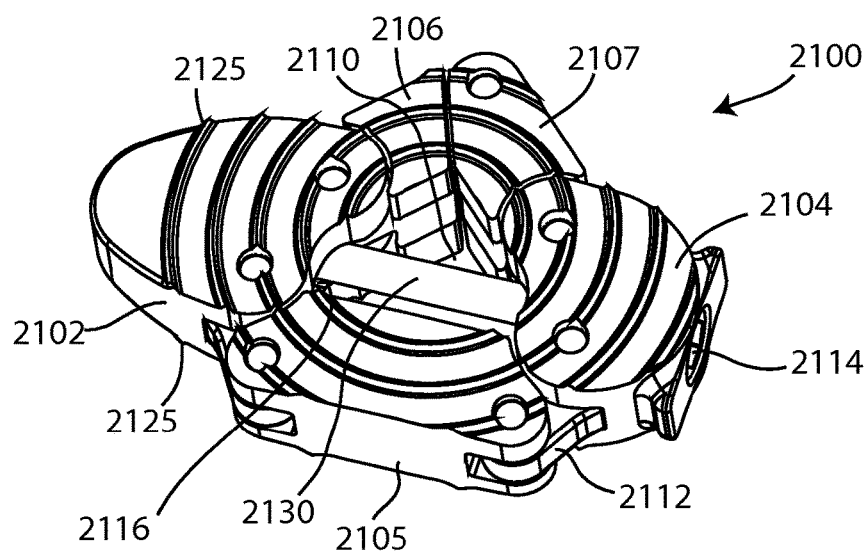
FIG. 18B is an isometric view of the device of FIG. 18A in an expanded configuration.

An alternate embodiment of an expanding fusion device, or implant, is shown in FIGS. 18A and 18B. FIG. 18A shows the implant in a compact configuration and FIG. 18B shows the implant in an expanded configuration. Referring now to FIGS. 18A and 18B, an expandable interbody device 2100 includes a first end body 2102, a second end body 2104, a first intermediate body 2105, a second intermediate body 2106, and a third intermediate body 2107. A central interior space 2110 occupies the area formed between the first and second end bodies, and between the first intermediate body 2105 and the second and third intermediate bodies 2106, 2107. A plurality of links 2112 connect the intermediate bodies to the end bodies, and may pivot to allow the interbody device 2100 to expand between the compact configuration shown in FIG. 18A and the fully expanded configuration shown in FIG. 18B. In the compact configuration, the volume of the central interior space 2110 is minimized, and in the fully expanded configuration the volume of the central interior space 2110 is maximized. The interbody device 2100 may be partially expanded along a continuum between the compact configuration and the fully expanded configuration, and the size of the central interior space 2110 expands accordingly along a continuum between a minimum volume and a maximum volume. Graft material may be inserted into the central interior space 2110 before, during and/or after implantation of the interbody device 2100 between two vertebral bodies.

A first channel 2114 extends from the exterior surface of the second end body 2104 through the second end body 2104 and opens into the central interior space 2110. In some embodiments, a second channel 2116 extends coaxially with the first channel 2114, from the central interior space 2110 and into the first end body 2102. Either or both of the first channel 2114 and the second channel 2116 may include interior shaping, or protrusions such as threads, for connection with other members or instrumentation for inserting, expanding and/or or locking the interbody device 2100.

The interbody device 2100 includes a superior side 2120, an inferior side 2122, and a peripheral wall 2124 extending between the superior and inferior sides 2120, 2122 and circumscribing the device 2100. The device 2100 further includes an anterior side 2126 and a posterior side 2128. The height of the peripheral wall 2124 between the superior and inferior sides 2120, 2122 may vary. For example, the posterior side 2128 may have a greater height than the anterior side 2126, providing a lordotic correction when the interbody device 2100 is inserted between two adjacent intervertebral bodies. A posterior side of the first intermediate body 2105 may be flat as shown in FIGS. 18A and 18B, to avoid impingement against the central canal and the spinal cord housed therein. A plurality of ridges 2125 protrude from the superior and inferior sides 2120, 2122 to aid in preventing expulsion. The ridges 2125 on the first and second end bodies 2102, 2104, and the first, second, and third intermediate bodies 2105, 2106, 2107 align to form a coherent pattern in the expanded configuration, although in the compact configuration, the ridges 2125 on at least some of the bodies may be misaligned.

A screw 2130 may extend through first channel 2114, across the central interior space 2110 and into second channel 2116 to move the interbody device 2100 between the compact and expanded configurations, and/or to lock the interbody device 2100 in the expanded position. Threads on screw 2130 may engage internal threads in second channel 2116 so that actuation of the screw 2130 in a first direction expands device 2100 toward the fully expanded configuration. The overall length of device 2100 along the screw axis may be shorter in the expanded configuration than in the compact configuration. The overall width (anterior to posterior) of the device 2100 may be wider in the expanded configuration than in the compact configuration.

Figure 19A:
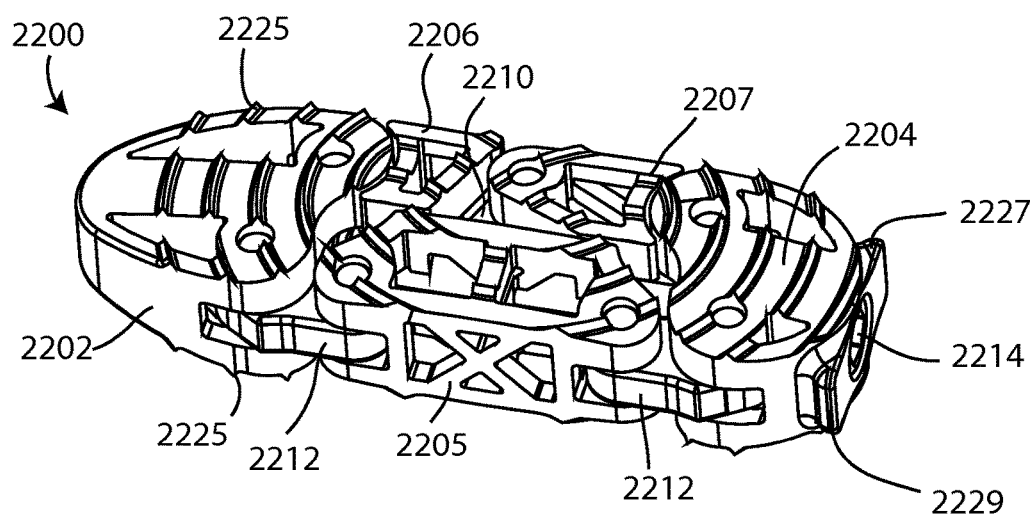
FIG. 19A is an isometric view of another expandable interbody device in a compact configuration.
Figure 19B:
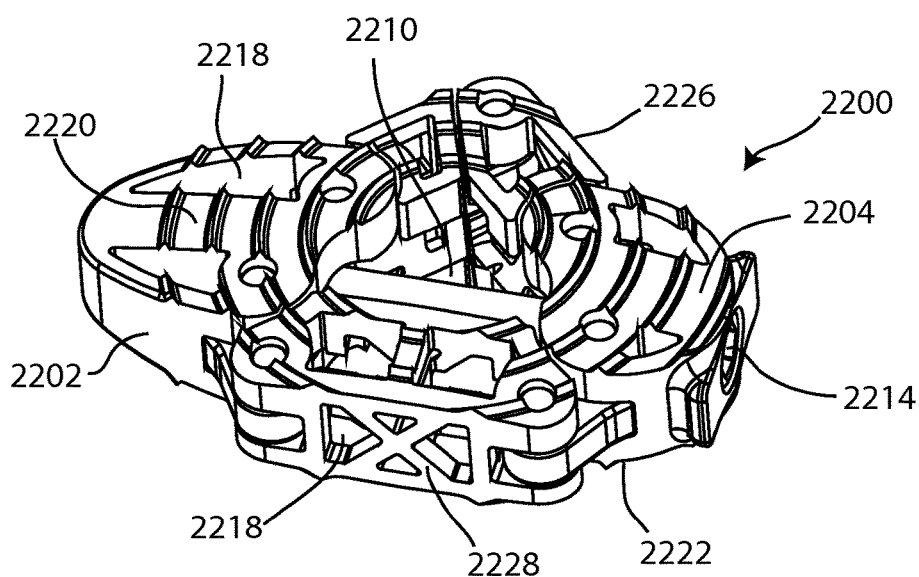
FIG. 19B is an isometric view of the device of FIG. 19A in an expanded configuration.

An alternate embodiment of an expanding fusion device, or implant, is shown in FIGS. 19A and 19B. Referring now to FIGS. 19A and 19B, an expandable interbody device 2200 includes a first end body 2202, a second end body 2204, a first intermediate body 2205, a second intermediate body 2206, and a third intermediate body 2207. A central interior space 2210 occupies the area formed between the first and second end bodies, and between the first intermediate body 2205 and the second and third intermediate bodies 2206, 2207. A plurality of links 2212 connect intermediate body 2205 to the end bodies, and pivot to allow the interbody device 2200 to expand between the compact configuration shown in FIG. 19A and the fully expanded configuration shown in FIG. 19B. Intermediate bodies 2206, 2207 are connected to one another and to end bodies 2202, 2204 by pivoting connections which are pins in the embodiment shown. In the compact configuration, the volume of the central interior space 2210 is minimized, and in the fully expanded configuration the volume of the central interior space 2210 is maximized. The interbody device may be partially expanded along a continuum between the compact configuration and the fully expanded configuration, and the size of the central interior space expands accordingly along a continuum between a minimum volume and a maximum volume. Graft material may be inserted into the central interior space 2210 before, during and/or after implantation of the interbody device 2200 between two vertebral bodies. In the expanded configuration, a screw 2400 may extend between the first and second end bodies 2202, 2204 to move the interbody device 2200 between the compact and expanded configurations, and/or to lock the device 2200 in the expanded configuration.

A first channel 2214 extends from the exterior surface of the second end body 2204 through the second end body 2204 and opens into the central interior space 2210. First channel 2214 may include an interior shoulder 2215 with a reduced inner diameter (FIG. 23B). In some embodiments, a second channel 2216 extends coaxially with the first channel 2214, from the central interior space 2210 and into the first end body 2202 (FIG. 22B). Either or both of the first and second channels 2214, 2216 may include interior shaping, or protrusions such as threads, for connection with screw 2400, other members or instrumentation for inserting, expanding and/or or locking the interbody device. A plurality of additional openings 2218 may be formed through the exterior surfaces of the links, end bodies and/or intermediate bodies. These openings 2218 allow for additional graft material to be packed into the interbody device 2200.

The interbody device 2200 includes a superior side 2220, an inferior side 2222, and a peripheral wall 2224 extending between the superior and inferior sides 2220, 2222 and circumscribing the device 2200. The device 2200 further includes an anterior side 2226 and a posterior side 2228. The height of the peripheral wall 2224 between the superior and inferior sides 2220, 2222 may vary. For example, the posterior side 2228 may have a greater height than the anterior side 2226, providing a lordotic correction when the interbody device 2200 is inserted between two adjacent intervertebral bodies. A posterior side of the first intermediate body 2205 may be flat as shown in FIGS. 19A and 19B, to avoid impingement against the central canal and the spinal cord housed therein. Exterior shoulders 2227, 2229 are formed on the device for connection with an insertion instrument. A plurality of ridges 2225 protrude from the superior and inferior sides 2220, 2222 to aid in preventing expulsion.

In other embodiments, interbody device 2100 or interbody device 2200 may have more or fewer than five body components. The number and distribution of links or other connecting features such as pins may vary accordingly. Either device 2100 and 2200 may include exterior ridges, grooves, teeth, surface roughening, porous coatings or other treatments which enhance fixation to bone and/or bone ingrowth or ongrowth. Either device 2100 and 2200 may further include one or more clamps, clips, clasps, braces, snapping mechanisms or other locking devices to hold the device in the compact configuration or in the expanded configuration. Such locking devices may be integral to the interbody device or may be entities separate from the interbody device. Either device 2100 and 2200 may further include one or more biasing elements to bias the device toward the compact configuration or toward the expanded configuration.

Interbody devices 2100 and 2200 may be made of PEEK (polyether ether ketone), titanium, stainless steel, cobalt chrome, ceramic, or other biologically compatible materials, or combinations of these materials. Interbody devices comprising PEEK may allow optimal visualization of the spinal column during and after surgery. Interbody devices comprising titanium may provide maximum strength while allowing the maximum volume of bone graft to be incorporated into the device. For example, numerous graft openings may be included in a titanium device while the device still provides the desired support between the vertebral bodies.

Figure 20:
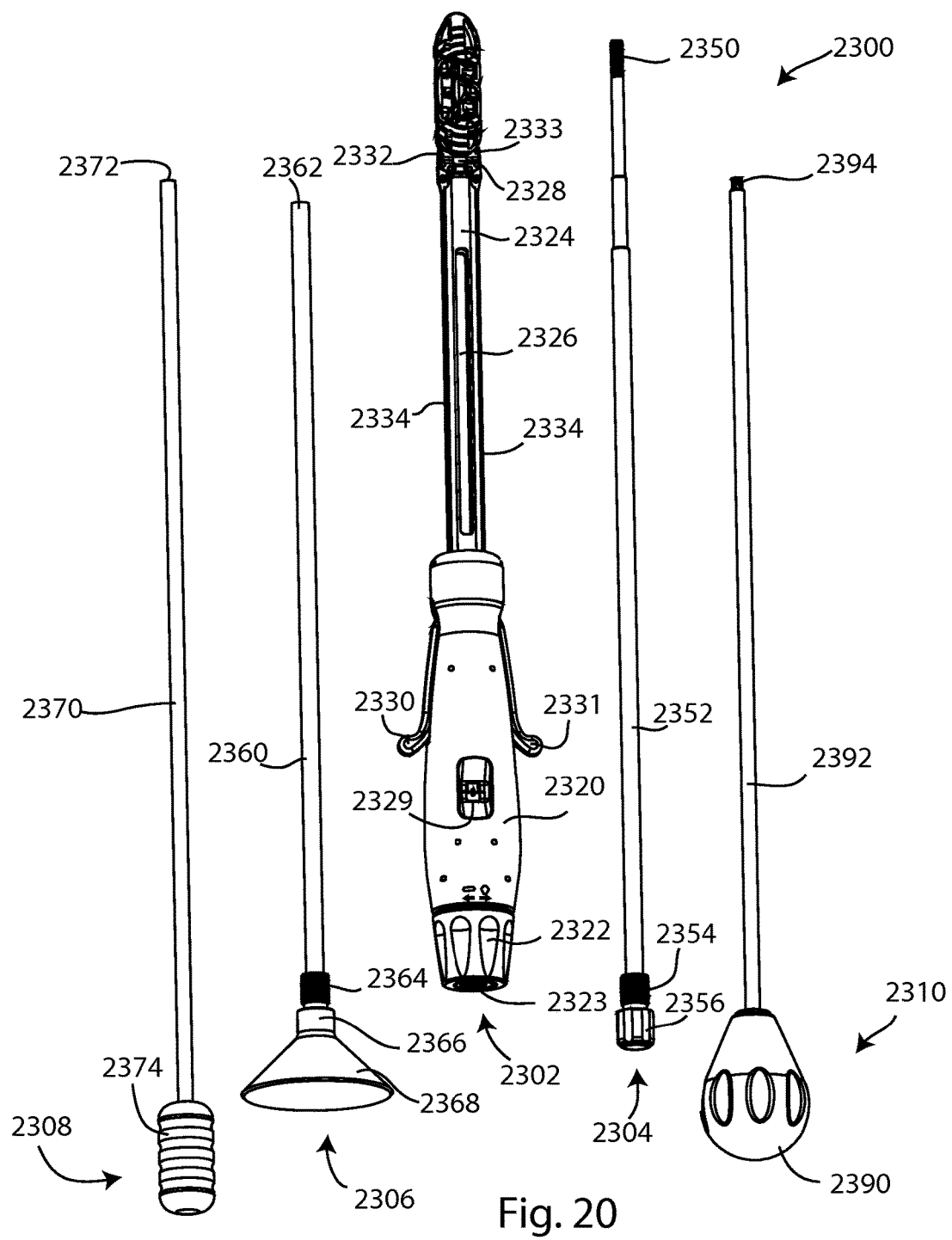
FIG. 20 is an isometric view of an instrument set for inserting, expanding, locking and filling the device of FIG. 20, the instrument set comprising an insertion instrument, a draw bar, a graft funnel, a graft tamp, and a screw driver.

Referring to FIG. 20, an alternate instrument set 2300 is depicted which may be used to implant the interbody devices 2100, 2200 and fill the devices with bone graft material in situ. Instrument set 2300 comprises a modular inserter instrument 2302, a draw bar 2304, a graft funnel 2306, a tamp 2308, and a driver 2310. Each interbody device 2100, 2200 may individually be rigidly mounted to the distal end of the inserter instrument 2302. Each of the draw bar 2304, graft funnel 2306, tamp 2308, and driver 2310 may be inserted partially through the inserter instrument 2302 to perform various functions with the mounted interbody device.

Referring to FIGS. 20, 21A and 21B, an alternate tool or inserter instrument 2302 includes a handle 2320, an actuator which may be an inserter knob 2322, and a cannulated inserter shaft 2324. The inserter knob 2322 includes a threaded receptacle 2323. At least one cutout 2326 may be formed into the shaft 2324 similar to the previous embodiment shaft 1004. An attachment port 2328 is formed on the distal end of the inserter shaft 2324. At least one indicator 2329 may be present on the instrument. The inserter instrument 2302 further includes first and second levers 2330, 2331 connected to first and second jaws 2332, 2333 via a pair of control bars 2334 which are received in grooves on the sides of the inserter shaft 2324. The control bars 2334 with the first and second levers 2330, 2331 may function in a manner similar to the first knob 1022 of the previous inserter embodiment, in that both function to actuate the first and jaws 2332, 2333. At the distal end of the inserter shaft 2324, the instrument includes a working end 2341 with an attachment or gripping mechanism 2340 for gripping, rigidly holding, and releasing an interbody device. Gripping mechanism 2340 includes the first and second jaws 2332, 2333. The second jaw 2333 may be a mirror image of the first jaw. Each jaw 2332, 2333 includes a jaw recess 2342 and a lip 2346. Each jaw 2322, 2333 is pivotably attached to the distal end of the inserter shaft at the attachment port 2328, and each jaw 2322, 2333 is pivotably attached to the distal end of a control bar 2334. When levers 2330, 2331 are lifted away from the handle 2320, jaws 2332, 2333 pivot outward from the attachment port 2328, as seen in FIG. 21A. When levers 2330, 2331 are moved toward the handle 2320, jaws 2332, 2333 pivot toward the attachment port 2328 and can grip an implant such as interbody device 2200, as seen in FIG. 21B.

Figure 22A:
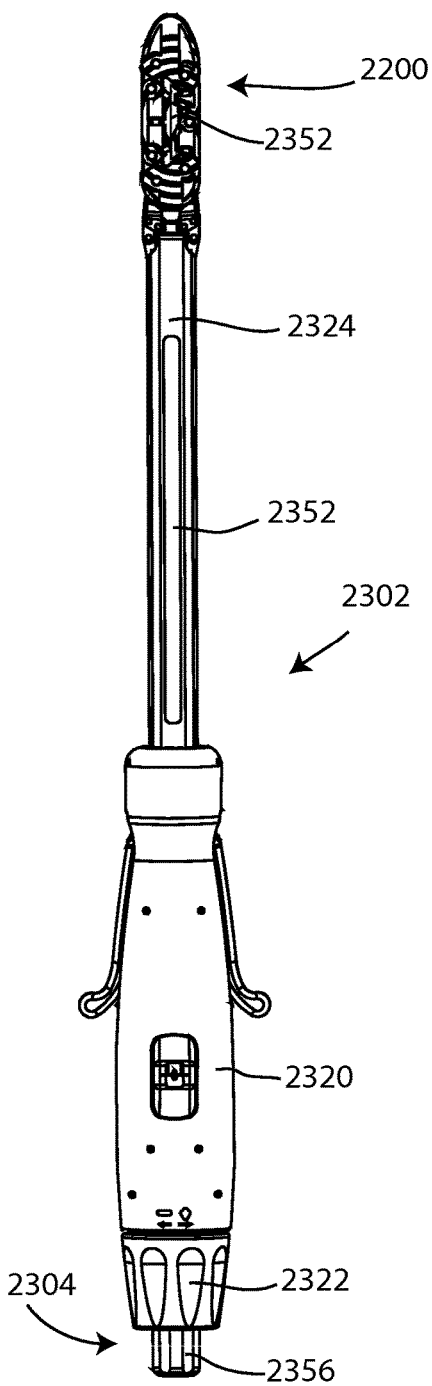
FIG. 22A is view of the insertion instrument and interbody device of FIG. 21A with the draw bar of FIG. 20 inserted through the instrument and engaged with the interbody device, the interbody device in the compact configuration.
Figure 22B:
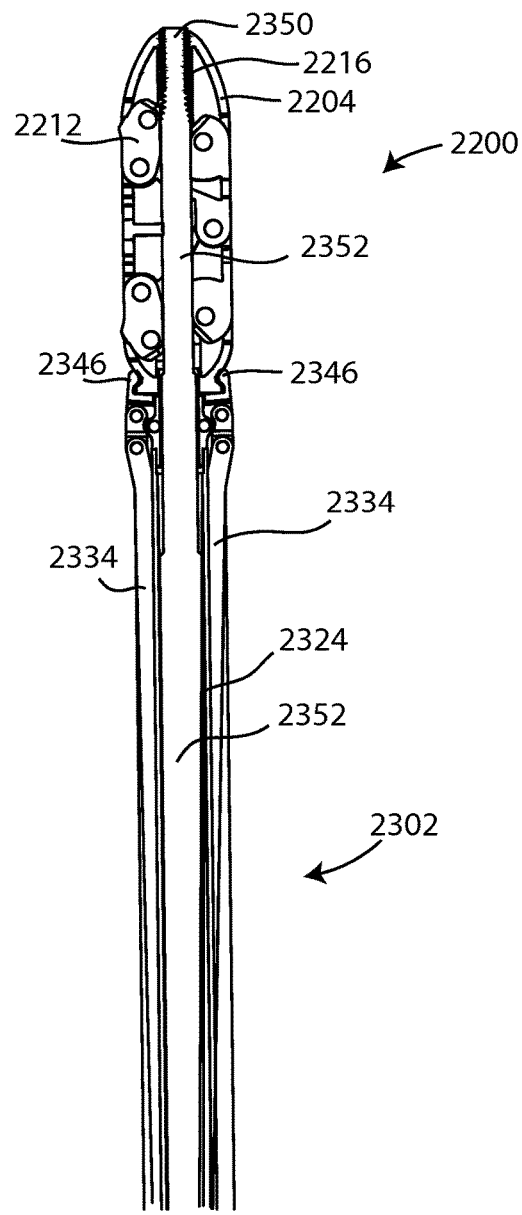
FIG. 22B is an enlarged cross-sectional view of the insertion instrument, draw bar and interbody device of FIG. 22A.
Figure 23A:
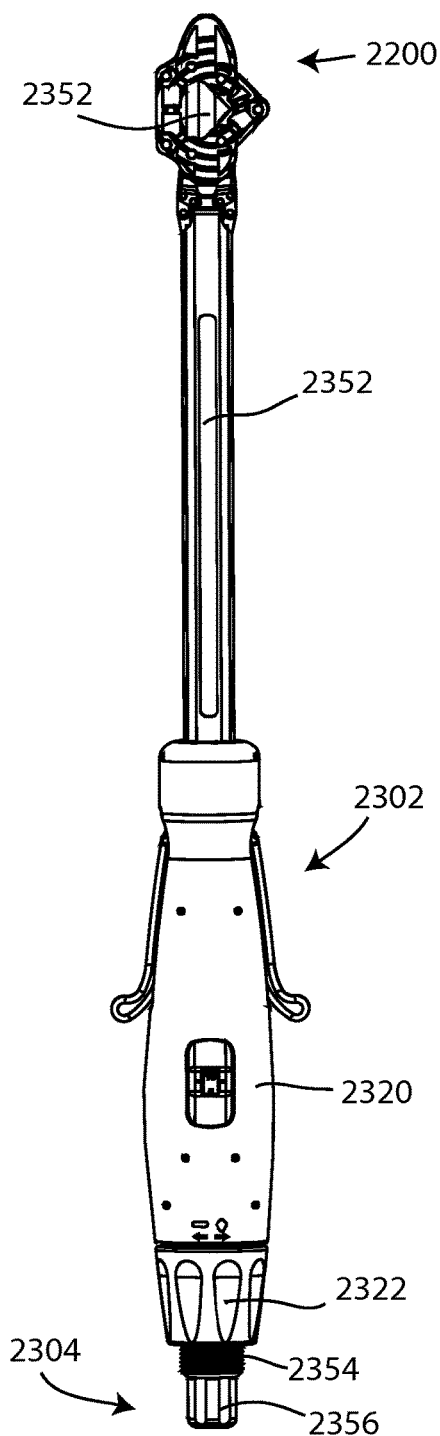
FIG. 23A is view of the insertion instrument and interbody device of FIG. 21A with the draw bar of FIG. 20 inserted through the instrument and engaged with the interbody device, the interbody device in the expanded configuration.
Figure 23B:
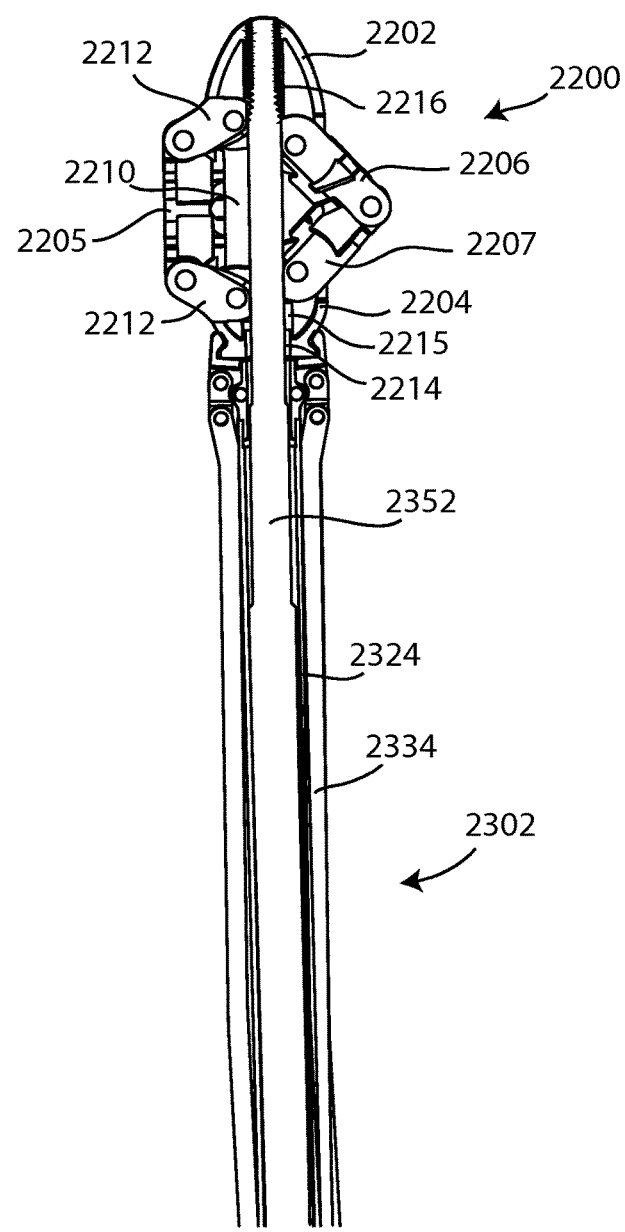
FIG. 23B is an enlarged cross-sectional view of the insertion instrument, draw bar and expanded interbody device of FIG. 23A.

Referring to FIGS. 20, and 22A-23B draw bar 2304 can be inserted through inserter instrument 2300 and actuated to move any of the interbody devices disclosed herein between the compact and expanded configurations. The draw bar 304 includes a distally located threaded tip 2350, a draw bar shaft 2352, a threaded receptacle portion 2354 at a proximal end, and a draw bar knob 2356. The draw bar shaft 2352 may include stepped portions. The threaded tip 2350 and receptacle portion 2354 may have equal pitch threads. In use, the draw bar 2304 is inserted into the inserter handle 2320 and shaft 2324, with tip 2350 extending into the interbody device 2200 through first channel 2214. When threaded tip 2350 reaches into second channel 2216, threaded receptacle portion 2354 enters threaded receptacle 2323 of the knob 2322. The draw bar is rotated so that threaded tip 2350 fully engages threaded second channel 2216 simultaneously with threaded receptacle portion 2354 fully engages threaded receptacle 2323, as seen in FIGS. 22A and 22B. The threads of tip 2350, second channel 2216, receptacle portion 2354, and receptacle 2323 are all rotationally oriented for simultaneous threading, and may be rotationally oriented for simultaneous initial engagement of tip 2350 in second channel 2216 and receptacle portion 2354 in receptacle 2323. Draw bar knob 2356 prevents over-insertion of the draw bar into the instrument 2300 and interbody device 2200. To expand the interbody device 2200, inserter knob 2322 is rotated counter-clockwise about draw bar 2304 to feed draw bar 2304 proximally, and thus draw, or pull the second end body 2202 of device 2200 toward the first end body 2204, as seen in FIG. 23B. The links 2212 pivot, urging intermediate body 2205 outward, and intermediate bodies 2206, 2207 pivot relative to one another to provide the expanded configuration. The volume of central interior space 2210 is increased by the expansion. Once the interbody device 2200 is expanded as desired, draw bar knob 2356 may be rotated counter-clockwise to disengage from device 2200 and threaded receptacle 2323, and draw bar 2304 may be withdrawn from the device 2200 and the inserter instrument 2300.

In another method of use, draw bar 2304 may be used to urge the device 2200 from the expanded to the compact configuration, and to remove the device 2200 from its implanted location. Inserter instrument 2302 may be engaged with device 2200 as described above, with jaws 2332, 2333 gripping device 2200. Draw bar 2304 may be inserted into and engaged with instrument 2302 and device 2200 as described previously. Inserter knob 2322 may then be rotated clockwise to urge draw bar 2304 distally, thus transforming the interbody device 2200 from the expanded configuration seen in FIG. 23B to the compact configuration seen in FIG. 22B. Inserter instrument 2302 may then be pulled proximally to remove the device 2200 from its implanted location.

Referring to FIGS. 20, 24A and 24B, graft funnel 2306 is insertable through inserter instrument 2302 to provide a passageway for packing bone graft or other material in and around an interbody device. Graft funnel 306 includes a funnel shaft 2360 which is cannulated and has a distal shaft opening 2362, a threaded receptacle portion 2364 at a proximal end, a funnel neck 2366 and a funnel head 2368. In a method of use, graft funnel 2306 is inserted into inserter instrument 2302 with funnel shaft 2360 extending through inserter shaft 2324, and shaft opening 2362 abutting attachment port 2328. Threaded receptacle portion 2364 engages with threaded receptacle 323 to hold the graft funnel 2306 in its inserted position. Funnel neck 366 may prevent over-insertion of the graft funnel 2306 into the instrument and interbody device. The inner diameters of first channel 2214, attachment port 328 and funnel shaft 2360 are equal, providing a smooth, uninterrupted path for graft material, and precluding any pockets or other inclusions where graft material could potentially hang up or be lost. Bone graft material is then fed into funnel head 2368, through funnel shaft 2360, attachment port 2328, first channel 2214 and deposited in the central interior space 2210 of the interbody device 2200. The graft material may fill the central interior space 2210 and spill over into one or more of the additional openings 2218, or across superior and/or inferior surfaces of the interbody device. The graft material may be pre-measured to ensure placement of a desired amount of material, or to calculate the actual amount of material placed.

Figure 25A:
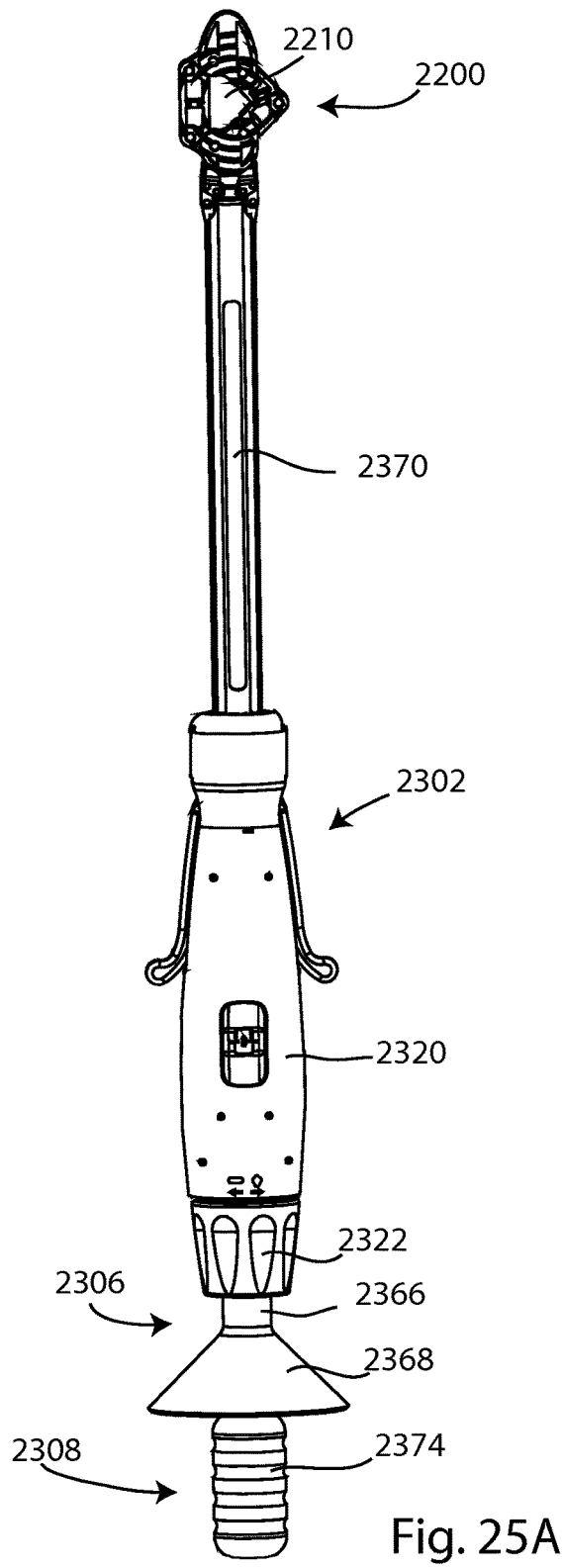
FIG. 25A is view of the insertion instrument and interbody device of FIG. 21A with the graft funnel and the tamp of FIG. 20 inserted through the instrument into a channel of the interbody device, the interbody device in the expanded configuration.
Figure 25B:
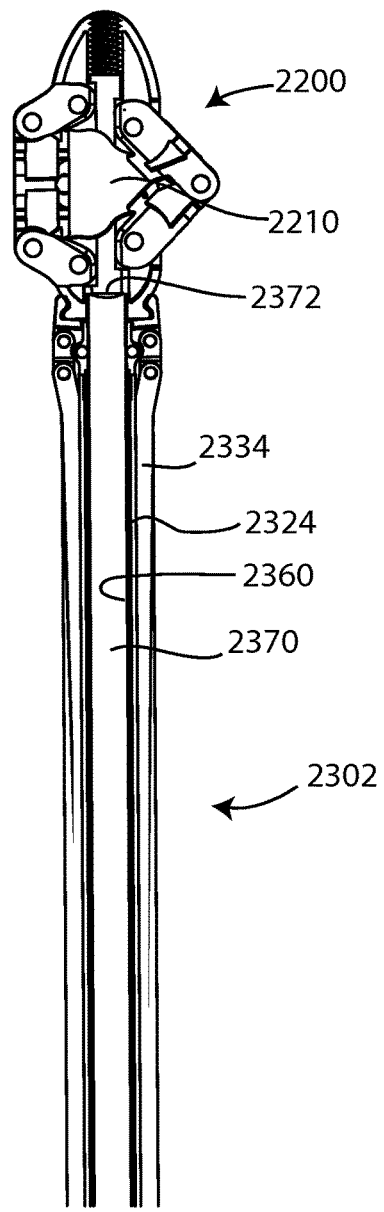
FIG. 25B is an enlarged cross-sectional view of the insertion instrument, graft funnel, tamp and interbody device of FIG. 25A.

As shown in FIGS. 20, 25A and 25B, the tamp 308 is insertable through the graft funnel 2306 to push and/or pack the bone graft material. The tamp 2308 includes a handle 2374, and a tamp shaft 2370 having a distal tip 2372. In the embodiment shown, distal tip 2372 is concave. In a method of use, the tamp 2308 is inserted into the graft funnel 2306 after placement of bone graft material in the funnel 2306. The tamp shaft 2370 is coaxially received in the cannulated funnel shaft 2360, and the distal tip 2372 pushes the graft material through the funnel shaft 2360, attachment port 2328, first channel 2214 and into the central interior space 2210. By extending all the way into the first channel 2214 of the interbody device 2200, the tamp 2108 may minimize graft waste. The concavity of tip 2372 minimizes graft insertion forces and collects graft from the interior of the funnel shaft 2360 as the tamp 2308 is passed through the graft funnel. The outer diameter of the tamp shaft 2370 and tip 2372 is smaller than the inner diameter of the funnel shaft 2360 with just enough clearance to allow movement of the tamp shaft 2370 through the funnel shaft 2360, but not enough space to permit loss of graft material between the tamp shaft 2370 and the funnel shaft 2360.

Figure 26A:
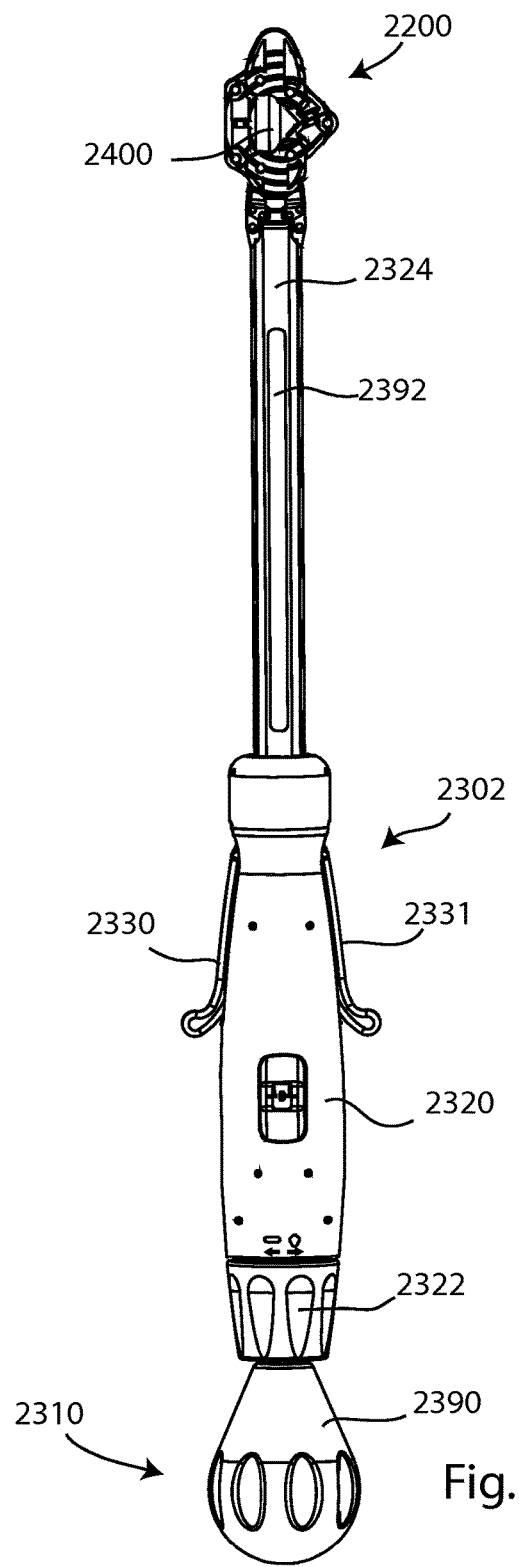
FIG. 26A is view of the insertion instrument and interbody device of FIG. 21A with a screw and the screwdriver of FIG. 20 inserted through the instrument into a channel of the interbody device, the interbody device in the expanded configuration.
Figure 26B:
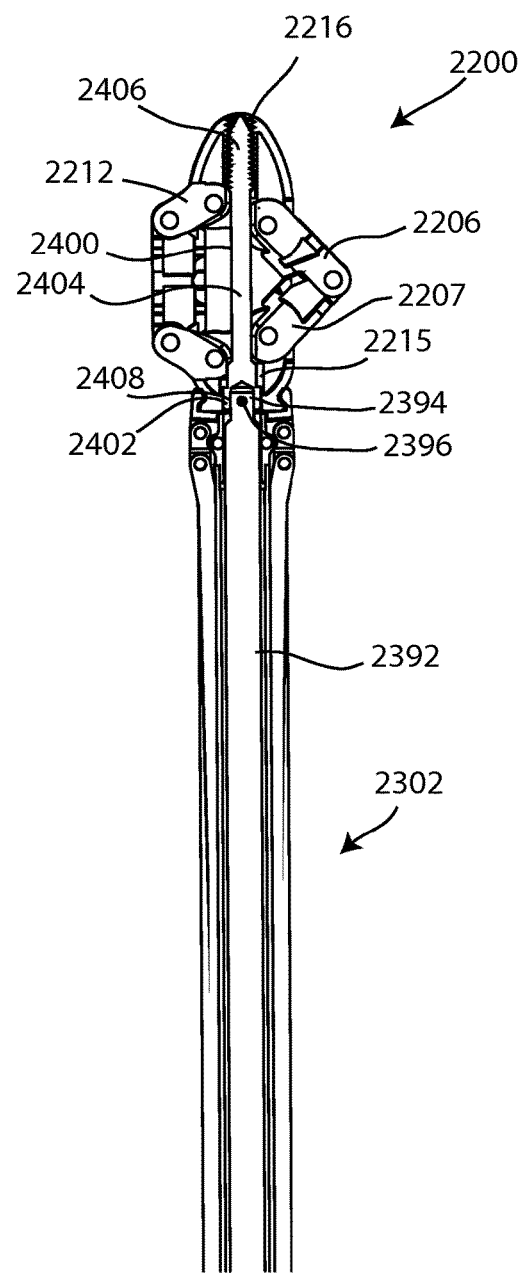
FIG. 26B is an enlarged cross-sectional view of the insertion instrument, screw, screwdriver and interbody device of FIG. 26A.

Referring to FIGS. 20, 26A and 26B, the driver 2310 is insertable through the inserter instrument 2302 to drive a screw 2400 into the interbody device 2200 to lock the interbody device 2200 in the expanded configuration. The driver 2310 includes a handle 2390, a driver shaft 2392, and a distal driver tip 2394. The distal driver tip 2394 is complementarily shaped to a drive feature on the screw 2400 so that when the driver tip 2394 is engaged with the screw, rotating the driver 2310 drives the screw. In the example shown, driver tip 2394 is hexagonal, but other shapes known in the art, including square, triangular, pentagonal, and star, are contemplated. At or adjacent the distal driver tip 2394, a retention feature 2396 may be present to assist in connection with the screw as the screw is placed and driven. Retention feature 2396 may be a ball detent as shown in FIG. 26B, taper, twist, spring feature, or other retention features known in the art.

Screw 2400 includes a head 2402, screw shaft 2404, and screw tip 2406. At least a portion of the screw tip and/or shaft is threaded. Head 2402 includes a drive feature 2408 which is complementarily shaped with the driver tip 2394 of the driver 2310. Screw tip 2406 may be bullet-nosed to promote easy passage through bone graft material.

With reference to FIGS. 21A-26B, in a method of use, instrument set 2300 is used to implant an interbody device in a patient's body between two bones, expand the device, and fill the device with bone graft material to promote fusion between the two bones. In this method, the interbody device 2200 is implanted into the intervertebral space between two adjacent vertebral bodies. An access passage is created along a lateral approach through the patient's body to the interbody space. The interbody device 2200 is rigidly attached to the inserter instrument 2302, with attachment port 2328 abutting and in communication with the first channel 2214, and jaws 2332, 2333 gripping shoulders 2229, 2227. In this rigidly mounted configuration, the interbody device 2200 is inserted along the lateral approach into the intervertebral space between the two adjacent vertebral bodies, with the superior side 2220 facing the superior vertebral body, and the inferior side 2222 facing the inferior vertebral body. The drawbar 2304 is inserted into the inserter instrument 2302 as described previously and shown in FIG. 22B, with threaded tip 2350 engaging threaded second channel 2216 simultaneously with threaded receptacle portion 354 engaging threaded receptacle 2323. The draw bar 2304 may be inserted into and engaged with the inserter instrument previous to insertion of the interbody device into the intervertebral space. Inserter knob 2322 is actuated to draw drawbar 2304 proximally and expand interbody device 2200 as shown in FIG. 23B. In the embodiment shown, the expansion of device 2200 is along the anterior and posterior directions, and device 2200 may decreases in length in the transverse, or medial/lateral, direction. The drawbar 2304 is disengaged and removed from the inserter instrument 2302. In other methods of use, for example if inserted along an anterior or posterior approach, the expansion may be along the medial/lateral direction while the device may decrease in length along the anterior/posterior direction.

Referring to FIGS. 24A and 24B, the graft funnel 2306 is inserted into the inserter instrument 2302. Bone graft material is placed into the funnel head 2368, passes through the funnel shaft 2360, through the attachment port 2328, into the interbody device 2200 and into the central interior space 2210. A mass of bone graft material may be deposited in the central interior space 2210. The tamp 2308 is inserted into the graft funnel 2306. Distal tip 2372 of the tamp pushes the bone graft material along the shaft and into the interbody device 2200 and central interior space 2210. The tamp 2308 and graft funnel 2306 are removed. Screw 2400 is inserted through the inserter instrument shaft 2324 toward the interbody device 2200. Screw 2400 may be retained to distal end of driver 2310. Driver 2310 is inserted through inserter instrument 2302, and the distal driver tip 2394 engages drive feature 2408 of screw head 2402. Screw 2400 is urged through the mass of bone graft material and screw tip 2406 engages the threaded second channel 2216. The interior surfaces of the links 2212 and the intermediate bodies 2206, 2207 guide the screw toward second channel 2216 to prevent cross-threading. Driver 2310 is actuated to turn screw 2400 to engage screw tip 2406 with the threaded second channel 2216. Screw head 2402 is retained by shoulder 2215 of first channel 2214, preventing over-insertion of screw 2400. Engagement of the screw 2400 with the interbody device 2200 locks the device 2200 in the expanded configuration. Driver 2310 is removed from inserter instrument 2302. Inserter instrument 2302 is disengaged from interbody device 2200 by moving levers 2330, 2331 to release jaws 2332, 2333 from the device 2200, and the inserter instrument 2302 is removed from the access passage.

Figure 27:
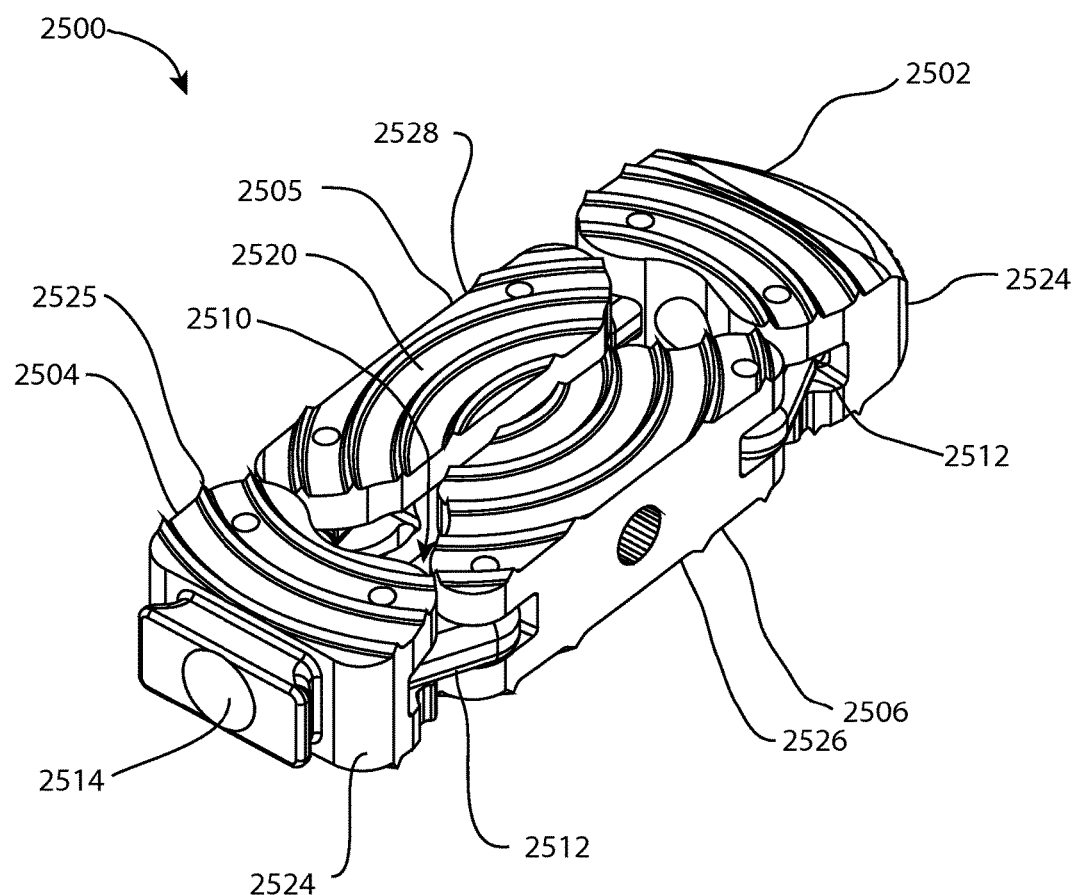
FIG. 27 is a perspective view of another expanding intervertebral fusion device in a compact configuration.
Figure 28:
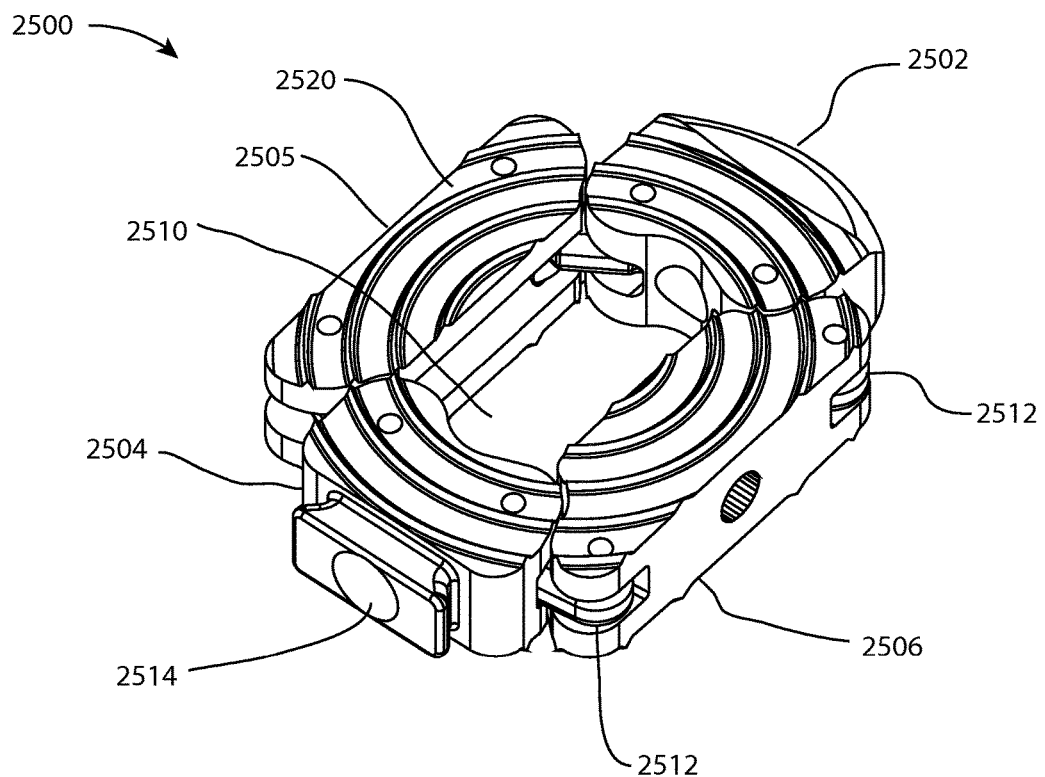
FIG. 28 is a perspective view of the fusion device of FIG. 27 in an expanded configuration.
Figure 29:
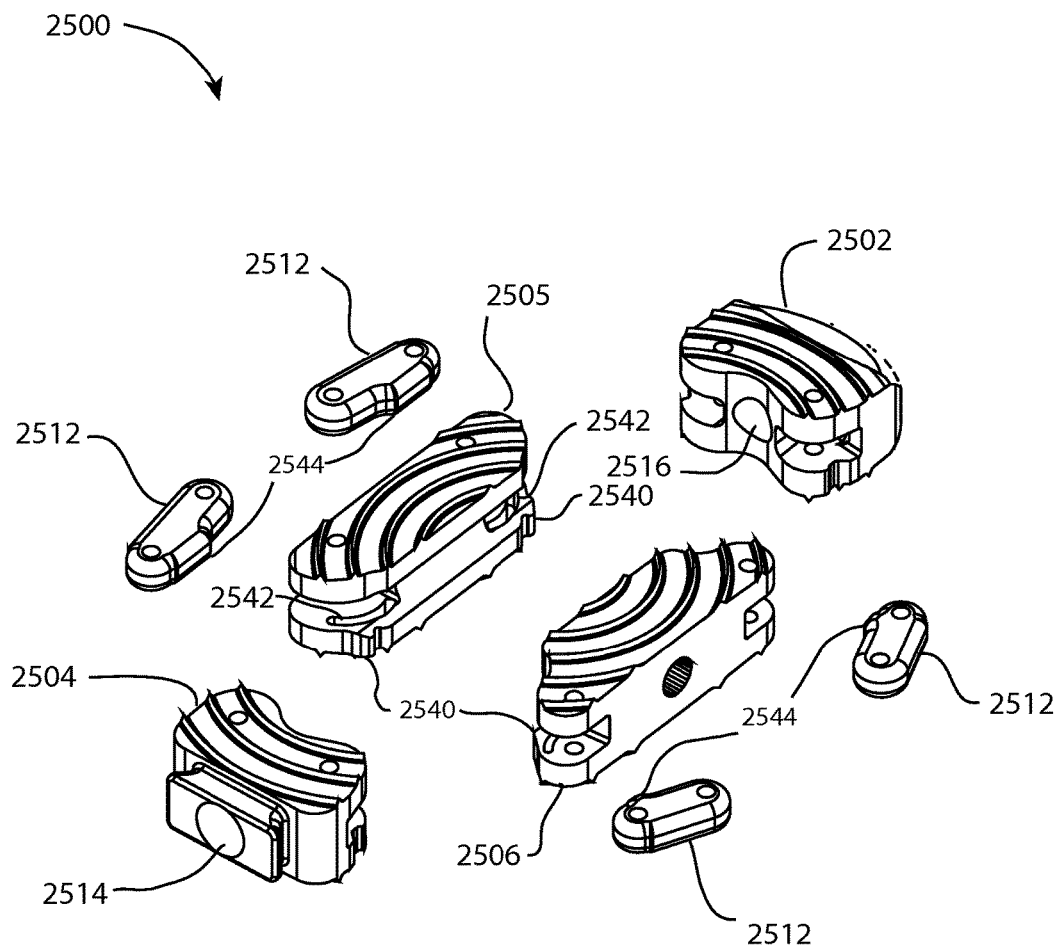
FIG. 29 is an exploded perspective view of the fusion device of FIG. 27.
Figure 30A:
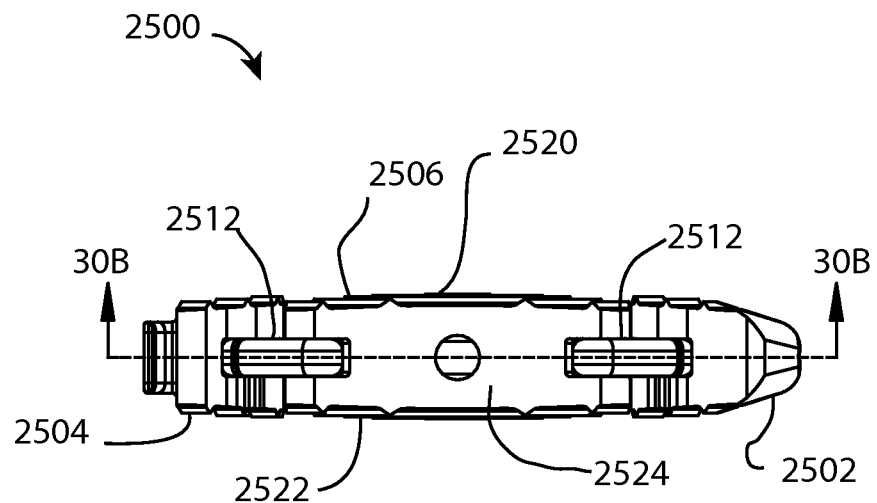
FIG. 30A is a side view of the fusion device of FIG. 27.
Figure 30B:
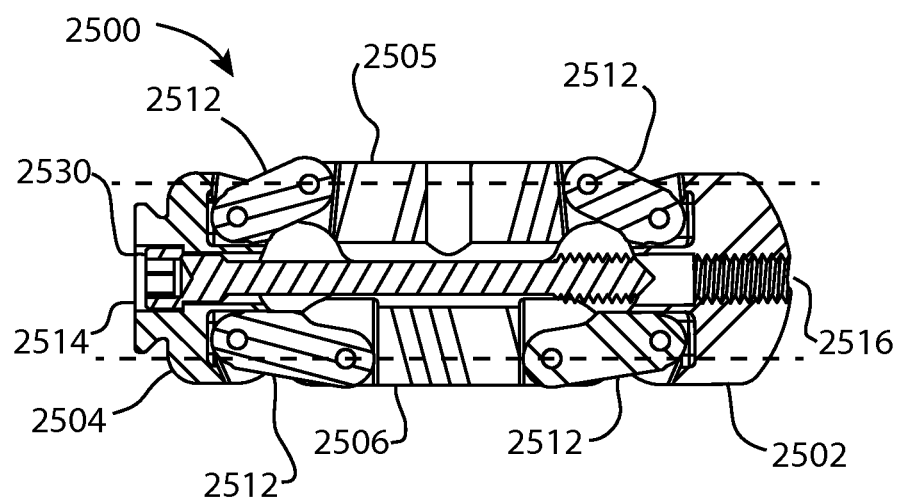
FIG. 30B is a cross section view of the fusion device of FIG. 27 taken along section line 30B-30B shown in FIG. 30A.
Figure 31A:
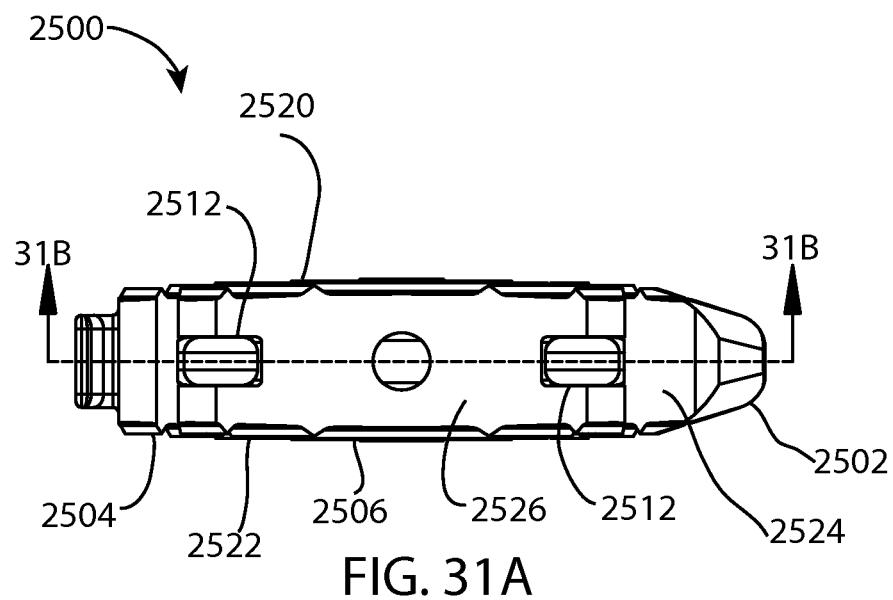
FIG. 31A is a side view of the fusion device of FIG. 28.
Figure 31B:
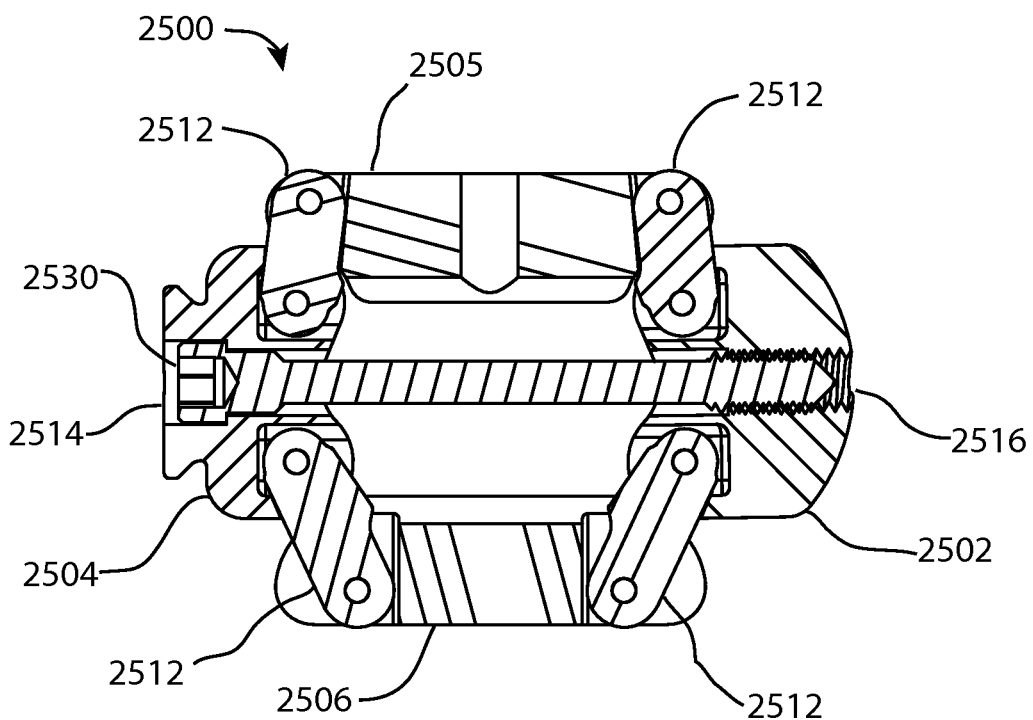
FIG. 31B is a cross section view of the fusion device of FIG. 28 taken along section line 31B-31B shown in FIG. 31A.

An alternate embodiment of an expanding fusion device, or implant, is shown in FIGS. 27-31B. FIGS. 27 and 30A-B show the implant in a compact configuration, FIG. 29 shows the implant in an exploded view, and FIGS. 28 and 31A-B show the implant in an expanded configuration. Referring now to 27 and 30A-B, an expandable interbody device 2500 includes a first end body 2502, a second end body 2504, a first intermediate body 2505 and a second intermediate body 2506. A central interior space 2510 occupies the area formed between the first and second end bodies, and between the first intermediate body 2505 and the second intermediate body 2506. A plurality of links 2512 connect the intermediate bodies to the end bodies, and may pivot to allow the interbody device 2500 to expand between the compact configuration shown in FIG. 27 and the fully expanded configuration shown in FIG. 28. In the compact configuration, the volume of the central interior space 2510 is minimized, and in the fully expanded configuration the volume of the central interior space 2510 is maximized. The interbody device 2500 may be partially expanded along a continuum between the compact configuration and the fully expanded configuration, and the size of the central interior space 2510 expands accordingly along a continuum between a minimum volume and a maximum volume. Graft material may be inserted into the central interior space 2510 before, during and/or after implantation of the interbody device 2500 between two vertebral bodies.

A first channel 2514 extends from the exterior surface of the second end body 2504 through the second end body 2504 and opens into the central interior space 2510. In some embodiments, a second channel 2516 extends coaxially with the first channel 2514, from the central interior space 2510 and into the first end body 2502. Either or both of the first channel 2514 and the second channel 2516 may include interior shaping, or protrusions such as threads, for connection with other members or instrumentation for inserting, expanding and/or or locking the interbody device 2500.

The interbody device 2500 includes a superior side 2520, an inferior side 2522, and a peripheral wall 2524 extending between the superior and inferior sides 2520, 2522 and circumscribing the device 2500. The device 2500 further includes an anterior side 2526 and a posterior side 2528. The height of the peripheral wall 2524 between the superior and inferior sides 2520, 2522 may vary. For example, the posterior side 2528 may have a greater height than the anterior side 2526, providing a lordotic correction when the interbody device 2500 is inserted between two adjacent intervertebral bodies. A posterior side of the first intermediate body 2505 may be flat as shown in FIGS. 27-31B, to avoid impingement against the central canal and the spinal cord housed therein. A plurality of ridges 2525 protrude from the superior and inferior sides 2520, 2522 to aid in preventing expulsion. The ridges 2525 on the first and second end bodies 2502, 2504, and the first, second, and third intermediate bodies 2505, 2506, 2507 align to form a coherent pattern in the expanded configuration, although in the compact configuration, the ridges 2525 on at least some of the bodies may be misaligned.

A screw 2530 may extend through first channel 2514, across the central interior space 2510 and into second channel 2516 to move the interbody device 2500 between the compact and expanded configurations, and/or to lock the interbody device 2500 in the expanded position. Threads on screw 2530 may engage internal threads in second channel 2516 so that actuation of the screw 2530 in a first direction expands device 2500 toward the fully expanded configuration. The overall length of device 2500 along the screw axis may be shorter in the expanded configuration than in the compact configuration. The overall width (anterior to posterior) of the device 2500 may be wider in the expanded configuration than in the compact configuration.

In other embodiments, interbody device 2500 may have more or fewer than four body components. The number and distribution of links or other connecting features such as pins may vary accordingly. Device 2500 may include exterior ridges, grooves, teeth, surface roughening, porous coatings or other treatments which enhance fixation to bone and/or bone ingrowth or ongrowth.

Device 2500 may further include one or more clamps, clips, clasps, braces, snapping mechanisms or other locking devices 2540 to hold the device in the compact configuration or in the expanded configuration. Such locking devices 2540 may be integral to the interbody device, as shown in FIG. 29, or may be entities separate from the interbody device. Device 2500 may further include one or more biasing elements to bias the device toward the compact configuration or toward the expanded configuration. The locking devices 2540 and biasing elements may be integrated together. The locking devices 2540 shown in FIG. 29 are integral cam features with slots 2542 to provide some flexibility or spring action. These locking devices 2540 may permit the device 2500 to transform between the compact configuration and the expanded configuration, but provide more resistance to transformation from the expanded configuration to the compact configuration than from the compact configuration to the expanded configuration. The locking devices 2540 function to hold the device 2500 in the expanded configuration.

Device 2500 may also include physical stops 2544 integrated into one or more of the links 2512. Similar to the interfaces 320, 620 mentioned earlier with regard to implant 100, the physical stops 2544 may limit the transformation of the device 2500 into the compact configuration or the expanded configuration, or both. The physical stops 2544 may encounter other portions of device 2500 which limit the range of motion of the affected link 2512 and thus the related bodies. In the example shown, the physical stops 2544 make contact with the first and second end bodies 2502, 2504 and/or first and second intermediate bodies 2505, 2506 to limit the transformation of the device 2500 into the compact configuration so that the pivot pins of first and second intermediate bodies 2505, 2506 stay lateral relative to the pivot pins of first and second end bodies 2502, 2504, as shown in FIG. 30B.

Interbody device 2500 may be made of PEEK (polyether ether ketone), titanium, stainless steel, cobalt chrome, ceramic, or other biologically compatible materials, or combinations of these materials. Interbody devices comprising PEEK may allow optimal visualization of the spinal column during and after surgery. Interbody devices comprising titanium may provide maximum strength while allowing the maximum volume of bone graft to be incorporated into the device. For example, numerous graft openings may be included in a titanium device while the device still provides the desired support between the vertebral bodies.

It should be understood that the present system, kits, apparatuses, and methods are not intended to be limited to the particular forms disclosed. Rather, they are to cover all modifications, equivalents, and alternatives falling within the scope of the claims. For example, while the present disclosure is made primarily in the context of spinal interbody fusion from a lateral approach, the implants, instruments, and methods disclosed herein are readily adaptable to spinal interbody fusion from any other approach direction, as well as being adaptable to other bone fusion scenarios, such as the fusion of bones at a joint, or bone fragments at an osteotomy, fracture, or other bony defect or discontinuity. One of skill in the art will appreciate that the directional terms used in the preceding description of the implants, instruments, and methods are all subject to change as a result of adapting the disclosed technology to these alternate uses.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, any fusion device disclosed herein may be implanted with any of the instrumentation or methods disclosed herein. Features of one fusion device may be applied to a fusion device from another example. Features of instrumentation from one example may be applied to instrumentation from another example. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An intervertebral system, comprising:
an interbody device comprising a plurality of linked bodies encircling a central interior space, the interbody device transformable between a compact configuration and an expanded configuration, the interbody device comprising a first channel and a second channel, the first channel extending from an exterior surface of the interbody device into the central interior space, the second channel extending from the central interior space into one of the plurality of linked bodies;
an inserter comprising a shaft portion, a cannulation, and an attachment mechanism which rigidly attaches the inserter to the interbody device;
a draw bar comprising a distal tip, a shaft, and a proximal end, wherein the draw bar is insertable through the cannulation of the inserter and the first channel of the interbody device and engageable with the second channel of the interbody device, wherein the draw bar transforms the interbody device between the compact configuration and the expanded configuration; and
a screw comprising a head, a screw shaft, and a screw tip, wherein the screw is insertable through the cannulation of the inserter and engageable with the first and second channels of the interbody device in the expanded configuration, wherein the screw locks the interbody device in the expanded configuration;
wherein when the inserter is attached to the interbody device, the draw bar is inserted through the cannulation of the inserter and the first channel of the interbody device, and the draw bar is engaged with the second channel of the interbody device, the first and second channels of the interbody device, the shaft portion of the inserter, and the shaft of the draw bar are coaxial and the distal tip of the draw bar engages the second channel of the interbody device;
wherein when the inserter is attached to the interbody device, the screw is inserted through the cannulation of the inserter, and the screw is engaged with the first and second channels of the interbody device in the expanded configuration, the first and second channels of the interbody device, the shaft portion of the inserter, and the screw shaft are coaxial, the head of the screw engages the first channel of the interbody device, and the screw tip engages the second channel of the interbody device to lock the interbody device in the expanded configuration.

2. The system of claim 1, wherein the inserter further comprises a first jaw and a second jaw, wherein the first and second jaws are mirror images, wherein the first jaw is pivotably connected to a first control bar and the second jaw is pivotably connected to a second control bar, wherein each control bar comprises a lever.

3. The system of claim 1, wherein the inserter further comprises a threaded inserter knob at a proximal end for receiving the draw bar, wherein the proximal end of the draw bar comprises proximal threads to engage the threaded inserter knob.

4. The system of claim 3, wherein the distal tip of the draw bar comprises distal threads of the same pitch as the proximal threads of the draw bar.

5. The system of claim 4, wherein when the draw bar proximal threads fully engage the threaded inserter knob the draw bar distal threads simultaneously fully engage the second channel of the interbody device.

6. The system of claim 3, wherein the first channel of the interbody device extends from an exterior surface of the interbody device into the central interior space through a first end body of the plurality of linked bodies, wherein the second channel of the interbody device extends into a second end body of the plurality of linked bodies, wherein the inserter knob is rotatable about the draw bar and when the inserter knob is rotated counter-clockwise, the draw bar pulls the second end body of the interbody device toward the first end body of the interbody device urging the interbody device from the compact configuration to the expanded configuration.

7. The system of claim 6, wherein the interbody device further comprises a first intermediate body and a second intermediate body, wherein the first and second intermediate bodies are closer to one another in the compact configuration and further apart in the expanded configuration.

8. The system of claim 7, further comprising a plurality of pivotable connections linking the first and second end bodies with the first and second intermediate bodies.

9. The system of claim 1, comprising a funnel insertable through the cannulation of the inserter to provide passage for graft material into the central interior space of the interbody device.

10. The system of claim 9, wherein the inserter further comprises a threaded inserter knob at a proximal end for receiving the funnel, wherein the funnel comprises proximal threads to engage the threaded inserter knob.

11. The system of claim 9, comprising a tamp insertable through a cannulated shaft of the funnel; wherein the tamp pushes the graft material through the cannulated shaft of the funnel and into the central interior space of the interbody device.

12. The system of claim 11, wherein when the tamp is inserted through the cannulated shaft of the funnel, the tamp is insertable into the first channel of the interbody device.

13. The system of claim 1, comprising a driver insertable through the cannulation of the inserter to drive the screw into the second channel of the interbody device.

14. The system of claim 1, wherein the interbody device further comprises at least one locking device to hold the interbody device in the expanded configuration.

15. The system of claim 1, wherein the interbody device comprises a plurality of openings formed through the exterior surface of the interbody device.

* * * * *